United States Patent
Garrido Fleury et al.

(10) Patent No.: US 12,070,452 B2
(45) Date of Patent: Aug. 27, 2024

(54) COMPOUNDS TARGETING HSP110 PROTEIN FOR CANCER TREATMENT

(71) Applicants: INSERM (Institut National de la Santé et de la Recherche Médicale), Paris (FR); Université de Caen Normandie, Caen (FR); Université de Bourgogne, Dijon (FR)

(72) Inventors: Carmen Garrido Fleury, Dijon (FR); Gaetan Jego, Dijon (FR); Daniel Gonzalez, Dijon (FR); Anne-Sophie Voisin-Chiret, Caen (FR)

(73) Assignees: INSERM (INSTITUT NATIONAL DE LA SANTÉ ET DE LA RECHERCHE MEDICALE), Paris (FR); UNIVERSITÉ DE CAEN NORMANDIE, Caen (FR); UNIVERSITÉ DE BOURGOGNE, Dijon (FR)

(*) Notice: Subject to any disclaimer, the term of this patent is extended or adjusted under 35 U.S.C. 154(b) by 687 days.

(21) Appl. No.: 17/265,716

(22) PCT Filed: Aug. 5, 2019

(86) PCT No.: PCT/EP2019/071022
§ 371 (c)(1),
(2) Date: Feb. 3, 2021

(87) PCT Pub. No.: WO2020/030589
PCT Pub. Date: Feb. 13, 2020

(65) Prior Publication Data
US 2021/0186941 A1  Jun. 24, 2021

(30) Foreign Application Priority Data

Aug. 6, 2018 (EP) ..................... 18306079
Jan. 24, 2019 (EP) ..................... 19305094

(51) Int. Cl.
*A61K 31/444* (2006.01)
*A61K 31/519* (2006.01)
(Continued)

(52) U.S. Cl.
CPC .......... *A61K 31/444* (2013.01); *A61K 31/519* (2013.01); *A61K 45/06* (2013.01); *A61P 35/04* (2018.01)

(58) Field of Classification Search
CPC .............................. A61K 31/444; A61P 35/04
See application file for complete search history.

(56) References Cited

U.S. PATENT DOCUMENTS 10,307,410 B2 * 6/2019 Poulain ................ C07D 213/58

FOREIGN PATENT DOCUMENTS

WO  2012/127062 A1  9/2012
WO  2015/132727 A1  9/2015

OTHER PUBLICATIONS

Berthenet et al.; "HSP110 promotes colorectal cancer growth through STAT3 activation"; Oncogene, vol. 36, No. 16, 2017, pp. 2328-2336.
(Continued)

*Primary Examiner* — Golam M Shameem
(74) *Attorney, Agent, or Firm* — WC&F IP

(57) ABSTRACT

HSP110 inhibitors bind directly to the nucleotide binding domain of HSP110 and then block the phosphorylation of STAT3, cancer cell growth or MyD88 stability. Aspects involve a compound of formula (I) for use in the treatment of a HSP110-associated cancer, for example colorectal cancer and lymphoma. An examplary compound was tested on a syngeneic model for which mouse colon cancer CT-26 cells were injected into Balb/c mice and on a NOD/SCID model in which mice were implanted with human colorectal cancer HCT116 cells. In those animals bearing a tumor, the compound induced tumor regression that was associated with the inhibition of other HSP110 reported tumorigenic functions (resistance to apoptosis, induction of pro-tumor macrophages). Further, the compound was tested on large B cell lymphoma cell lines (DLBCL) and it was able to alter the interaction between HSP110 and MyD88, which induces a degradation of the oncogene MyD88. Additionally, it has been shown that the compound acts synergistically with other anti-cancer agents, including with tyrosine kinase inhibitors like Ibrutinib.

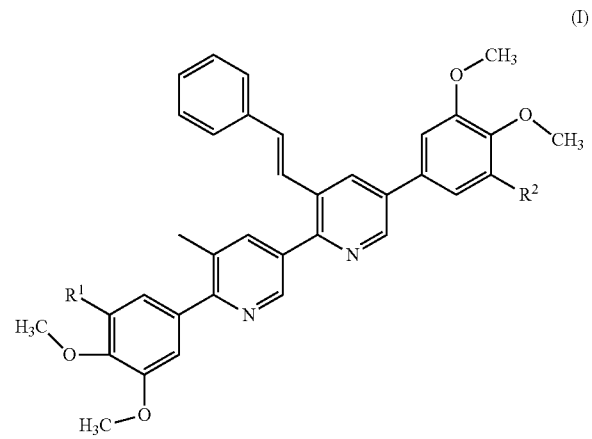

14 Claims, 16 Drawing Sheets
Specification includes a Sequence Listing.

(51) Int. Cl.
   *A61K 45/06*   (2006.01)
   *A61P 35/04*   (2006.01)

(56) References Cited

OTHER PUBLICATIONS

Granato et al.; "Tyrosine kinase inhibitor tyrphostin AG490 triggers both apoptosis and authophagy by reducing HSF1 and Mcl-1in PEL cells"; Cancer Letters, vol. 366, No. 2, Jul. 13, 2015, pp. 191-197.
Zhao et al.; "17-Demethoxy-reblastatin, an Hsp90 inhibitor, induces mitochondria-mediated apoptosis through downregulation of Mcl-1 in human hepatocellular carcinoma cells"; Journal of Bioenergetics and Biomembranes, vol. 47, No. 5, Sep. 1, 2015, pp. 373-381.

* cited by examiner

SEQUENCE LISTING

```
<160> NUMBER OF SEQ ID NOS: 9

<210> SEQ ID NO 1
<211> LENGTH: 858
<212> TYPE: PRT
<213> ORGANISM: Homo sapiens
<223> OTHER INFORMATION: "Full sequence of HSP110 protein"
<220> FEATURE:
<223> OTHER INFORMATION: Full sequence of HSP110 protein

<400> SEQUENCE: 1

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
                20                  25                  30

Arg Cys Thr Pro Ser Val Ile Ser Phe Gly Ser Lys Asn Arg Thr Ile
            35                  40                  45

Gly Val Ala Ala Lys Asn Gln Gln Ile Thr His Ala Asn Asn Thr Val
        50                  55                  60

Ser Asn Phe Lys Arg Phe His Gly Arg Ala Phe Asn Asp Pro Phe Ile
65                  70                  75                  80

Gln Lys Glu Lys Glu Asn Leu Ser Tyr Asp Leu Val Pro Leu Lys Asn
                85                  90                  95

Gly Gly Val Gly Ile Lys Val Met Tyr Met Gly Glu Glu His Leu Phe
            100                 105                 110

Ser Val Glu Gln Ile Thr Ala Met Leu Leu Thr Lys Leu Lys Glu Thr
        115                 120                 125

Ala Glu Asn Ser Leu Lys Lys Pro Val Thr Asp Cys Val Ile Ser Val
    130                 135                 140

Pro Ser Phe Phe Thr Asp Ala Glu Arg Arg Ser Val Leu Asp Ala Ala
145                 150                 155                 160

Gln Ile Val Gly Leu Asn Cys Leu Arg Leu Met Asn Asp Met Thr Ala
                165                 170                 175

Val Ala Leu Asn Tyr Gly Ile Tyr Lys Gln Asp Leu Pro Ser Leu Asp
            180                 185                 190

Glu Lys Pro Arg Ile Val Val Phe Val Asp Met Gly His Ser Ala Phe
        195                 200                 205

Gln Val Ser Ala Cys Ala Phe Asn Lys Gly Lys Leu Lys Val Leu Gly
    210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
                245                 250                 255
```

```
Lys Ser Lys Ile Arg Ala Leu Leu Arg Leu Tyr Gln Glu Cys Glu Lys
            260                 265                 270

Leu Lys Lys Leu Met Ser Ser Asn Ser Thr Asp Leu Pro Leu Asn Ile
275                 280                 285

Glu Cys Phe Met Asn Asp Lys Asp Val Ser Gly Lys Met Asn Arg Ser
            290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
                325                 330                 335

Ala Val Glu Ile Val Gly Gly Ala Thr Arg Ile Pro Ala Val Lys Glu
            340                 345                 350

Arg Ile Ala Lys Phe Phe Gly Lys Asp Ile Ser Thr Thr Leu Asn Ala
355                 360                 365

Asp Glu Ala Val Ala Arg Gly Cys Ala Leu Gln Cys Ala Ile Leu Ser
            370                 375                 380

Pro Ala Phe Lys Val Arg Glu Phe Ser Val Thr Asp Ala Val Pro Phe
385                 390                 395                 400

Pro Ile Ser Leu Ile Trp Asn His Asp Ser Glu Asp Thr Glu Gly Val
                405                 410                 415

His Glu Val Phe Ser Arg Asn His Ala Ala Pro Phe Ser Lys Val Leu
            420                 425                 430

Thr Phe Leu Arg Arg Gly Pro Phe Glu Leu Glu Ala Phe Tyr Ser Asp
                435                 440                 445

Pro Gln Gly Val Pro Tyr Pro Glu Ala Lys Ile Gly Arg Phe Val Val
450                 455                 460

Gln Asn Val Ser Ala Gln Lys Asp Gly Glu Lys Ser Arg Val Lys Val
465                 470                 475                 480

Lys Val Arg Val Asn Thr His Gly Ile Phe Thr Ile Ser Thr Ala Ser
                485                 490                 495

Met Val Glu Lys Val Pro Thr Glu Glu Asn Glu Met Ser Ser Glu Ala
            500                 505                 510

Asp Met Glu Cys Leu Asn Gln Arg Pro Pro Glu Asn Pro Asp Thr Asp
            515                 520                 525

Lys Asn Val Gln Gln Asp Asn Ser Glu Ala Gly Thr Gln Pro Gln Val
530                 535                 540

Gln Thr Asp Ala Gln Gln Thr Ser Gln Ser Pro Ser Pro Glu Leu
545                 550                 555                 560

Thr Ser Glu Glu Asn Lys Ile Pro Asp Ala Asp Lys Ala Asn Glu Lys
            565                 570                 575

Lys Val Asp Gln Pro Pro Glu Ala Lys Lys Pro Lys Ile Lys Val Val
                580                 585                 590

Asn Val Glu Leu Pro Ile Glu Ala Asn Leu Val Trp Gln Leu Gly Lys
            595                 600                 605

Asp Leu Leu Asn Met Tyr Ile Glu Thr Glu Gly Lys Met Ile Met Gln
610                 615                 620

Asp Lys Leu Glu Lys Glu Arg Asn Asp Ala Lys Asn Ala Val Glu Glu
625                 630                 635                 640

Tyr Val Tyr Glu Phe Arg Asp Lys Leu Cys Gly Pro Tyr Glu Lys Phe
                645                 650                 655

Ile Cys Glu Gln Asp His Gln Asn Phe Leu Arg Leu Leu Thr Glu Thr
            660                 665                 670

Glu Asp Trp Leu Tyr Glu Glu Gly Glu Asp Gln Ala Lys Gln Ala Tyr
```

```
                675                 680                 685
Val Asp Lys Leu Glu Glu Leu Met Lys Ile Gly Thr Pro Val Lys Val
690                 695                 700

Arg Phe Gln Glu Ala Glu Arg Pro Lys Met Phe Glu Glu Leu Gly
705                 710                 715                 720

Gln Arg Leu Gln His Tyr Ala Lys Ile Ala Ala Asp Phe Arg Asn Lys
                725                 730                 735

Asp Glu Lys Tyr Asn His Ile Asp Glu Ser Glu Met Lys Lys Val Glu
                740                 745                 750

Lys Ser Val Asn Glu Val Met Glu Trp Met Asn Asn Val Met Asn Ala
                755                 760                 765

Gln Ala Lys Lys Ser Leu Asp Gln Asp Pro Val Val Arg Ala Gln Glu
770                 775                 780

Ile Lys Thr Lys Ile Lys Glu Leu Asn Asn Thr Cys Glu Pro Val Val
785                 790                 795                 800

Thr Gln Pro Lys Pro Lys Ile Glu Ser Pro Lys Leu Glu Arg Thr Pro
                805                 810                 815

Asn Gly Pro Asn Ile Asp Lys Lys Glu Glu Asp Leu Glu Asp Lys Asn
                820                 825                 830

Asn Phe Gly Ala Glu Pro His Gln Asn Gly Glu Cys Tyr Pro Asn
                835                 840                 845

Glu Lys Asn Ser Val Asn Met Asp Leu Asp
850                 855

<210> SEQ ID NO 2
<211> LENGTH: 378
<212> TYPE: PRT
<213> ORGANISM: Homo sapiens
<223> OTHER INFORMATION: "Amino acids 1 to 378 of SEQ ID NO: 1 (ATP
      binding domain)"
<220> FEATURE:
<223> OTHER INFORMATION: Amino acids 1 to 378 of SEQ ID NO: 1 (ATP
      binding domain)

<400> SEQUENCE: 2

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
                20                  25                  30

Arg Cys Thr Pro Ser Val Ile Ser Phe Gly Ser Lys Asn Arg Thr Ile
                35                  40                  45

Gly Val Ala Ala Lys Asn Gln Gln Ile Thr His Ala Asn Asn Thr Val
                50                  55                  60

Ser Asn Phe Lys Arg Phe His Gly Arg Ala Phe Asn Asp Pro Phe Ile
65                  70                  75                  80

Gln Lys Glu Lys Glu Asn Leu Ser Tyr Asp Leu Val Pro Leu Lys Asn
                85                  90                  95

Gly Gly Val Gly Ile Lys Val Met Tyr Met Gly Glu Glu His Leu Phe
                100                 105                 110

Ser Val Glu Gln Ile Thr Ala Met Leu Leu Thr Lys Leu Lys Glu Thr
                115                 120                 125

Ala Glu Asn Ser Leu Lys Lys Pro Val Thr Asp Cys Val Ile Ser Val
                130                 135                 140

Pro Ser Phe Phe Thr Asp Ala Glu Arg Arg Ser Val Leu Asp Ala Ala
145                 150                 155                 160

Gln Ile Val Gly Leu Asn Cys Leu Arg Leu Met Asn Asp Met Thr Ala
```

-continued

```
                165                 170                 175
Val Ala Leu Asn Tyr Gly Ile Tyr Lys Gln Asp Leu Pro Ser Leu Asp
            180                 185                 190

Glu Lys Pro Arg Ile Val Val Phe Val Asp Met Gly His Ser Ala Phe
        195                 200                 205

Gln Val Ser Ala Cys Ala Phe Asn Lys Gly Lys Leu Lys Val Leu Gly
    210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
            245                 250                 255

Lys Ser Lys Ile Arg Ala Leu Leu Arg Leu Tyr Gln Glu Cys Glu Lys
        260                 265                 270

Leu Lys Lys Leu Met Ser Ser Asn Ser Thr Asp Leu Pro Leu Asn Ile
    275                 280                 285

Glu Cys Phe Met Asn Asp Lys Asp Val Ser Gly Lys Met Asn Arg Ser
290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
            325                 330                 335

Ala Val Glu Ile Val Gly Gly Ala Thr Arg Ile Pro Ala Val Lys Glu
        340                 345                 350

Arg Ile Ala Lys Phe Phe Gly Lys Asp Ile Ser Thr Thr Leu Asn Ala
    355                 360                 365

Asp Glu Ala Val Ala Arg Gly Cys Ala Leu
    370                 375

<210> SEQ ID NO 3
<211> LENGTH: 10
<212> TYPE: PRT
<213> ORGANISM: Homo sapiens
<223> OTHER INFORMATION: "Amino acids 184 to 193 of SEQ ID NO: 1"
<220> FEATURE:
<223> OTHER INFORMATION: Amino acids 184 to 193 of SEQ ID NO: 1

<400> SEQUENCE: 3

Tyr Lys Gln Asp Leu Pro Ser Leu Asp Glu
1               5                   10

<210> SEQ ID NO 4
<211> LENGTH: 10
<212> TYPE: PRT
<213> ORGANISM: Homo sapiens
<223> OTHER INFORMATION: "Amino acids 275 to 284 of SEQ ID NO: 1"
<220> FEATURE:
<223> OTHER INFORMATION: Amino acids 275 to 284 of SEQ ID NO: 1

<400> SEQUENCE: 4
```

```
Lys Leu Met Ser Ser Asn Ser Thr Asp Leu
1               5                   10

<210> SEQ ID NO 5
<211> LENGTH: 15
<212> TYPE: PRT
<213> ORGANISM: Homo sapiens
<223> OTHER INFORMATION: "Amino acids 341 to 355 of SEQ ID NO: 1"
<220> FEATURE:
<223> OTHER INFORMATION: Amino acids 341 to 355 of SEQ ID NO: 1

<400> SEQUENCE: 5

Val Gly Gly Ala Thr Arg Ile Pro Ala Val Lys Glu Arg Ile Ala
1               5                   10                  15

<210> SEQ ID NO 6
<211> LENGTH: 5
<212> TYPE: PRT
<213> ORGANISM: Homo sapiens
<223> OTHER INFORMATION: "Amino acids 360 to 364 of SEQ ID NO: 1"
<220> FEATURE:
<223> OTHER INFORMATION: Amino acids 360 to 364 of SEQ ID NO: 1

<400> SEQUENCE: 6

Lys Asp Ile Ser Thr
1               5

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer for WT HSP110
<220> FEATURE:
<223> OTHER INFORMATION: Primer for WT HSP110

<400> SEQUENCE: 7
gctacacgaa ttccagctgt ga                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic Reverse primer for HSP110
<220> FEATURE:
<223> OTHER INFORMATION: Reverse primer for HSP110

<400> SEQUENCE: 8
gagcagcatg gtttcgacta aa                                          22

<210> SEQ ID NO 9
<211> LENGTH: 380
<212> TYPE: PRT
<213> ORGANISM: Homo sapiens
<223> OTHER INFORMATION: "Truncated HSP110 protein"
<220> FEATURE:
<223> OTHER INFORMATION: Truncated HSP110 protein

<400> SEQUENCE: 9

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
                20                  25                  30

Arg Cys Thr Pro Ser Val Ile Ser Phe Gly Ser Lys Asn Arg Thr Ile
            35                  40                  45
```

```
Gly Val Ala Ala Lys Asn Gln Gln Ile Thr His Ala Asn Asn Thr Val
        50                  55                  60

Ser Asn Phe Lys Arg Phe His Gly Arg Ala Phe Asn Asp Pro Phe Ile
 65                  70                  75                  80

Gln Lys Glu Lys Glu Asn Leu Ser Tyr Asp Leu Val Pro Leu Lys Asn
                 85                  90                  95

Gly Gly Val Gly Ile Lys Val Met Tyr Met Gly Glu His Leu Phe
                100                 105                 110

Ser Val Glu Gln Ile Thr Ala Met Leu Leu Thr Lys Leu Lys Glu Thr
                115                 120                 125

Ala Glu Asn Ser Leu Lys Lys Pro Val Thr Asp Cys Val Ile Ser Val
        130                 135                 140

Pro Ser Phe Phe Thr Asp Ala Glu Arg Ser Val Leu Asp Ala Ala
145                 150                 155                 160

Gln Ile Val Gly Leu Asn Cys Leu Arg Leu Met Asn Asp Met Thr Ala
                165                 170                 175

Val Ala Leu Asn Tyr Gly Ile Tyr Lys Gln Asp Leu Pro Ser Leu Asp
                180                 185                 190

Glu Lys Pro Arg Ile Val Val Phe Val Asp Met Gly His Ser Ala Phe
                195                 200                 205

Gln Val Ser Ala Cys Ala Phe Asn Lys Gly Lys Leu Lys Val Leu Gly
        210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
                245                 250                 255

Lys Ser Lys Ile Arg Ala Leu Leu Arg Leu Tyr Gln Glu Cys Glu Lys
                260                 265                 270

Leu Lys Lys Leu Met Ser Ser Asn Ser Thr Asp Leu Pro Leu Asn Ile
                275                 280                 285

Glu Cys Phe Met Asn Asp Lys Asp Val Ser Gly Lys Met Asn Arg Ser
                290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
                325                 330                 335

Ala Val Glu Ile Val Gly Gly Ala Thr Arg Ile Pro Ala Val Lys Glu
                340                 345                 350

Arg Ile Ala Lys Phe Phe Gly Lys Asp Ile Ser Thr Thr Leu Asn Ala
                355                 360                 365

Asp Glu Ala Val Ala Arg Gly Cys Ala Leu Gln Cys
        370                 375                 380
```

COMPOUNDS TARGETING HSP110 PROTEIN FOR CANCER TREATMENT

FIELD OF THE DISCLOSURE

The present invention relates to the field of cancer treatment.

BACKGROUND OF THE DISCLOSURE

Cancer is a disease which involves an abnormal cell growth and most of the time invasion in different parts of the body, due to an avoidance of programmed cell death, also named apoptosis. Apoptosis is a complicated ordered process, usually activate for inducing cell death of aged cells or damaged cells. Many proteins are involved in this process, some allowing the activation of the pathways and others raising a negative regulation.

Heat shock proteins (HSP) are a class of functionally related proteins, called chaperone proteins, whose expression is increased when cells are exposed to different stress (such as elevated temperature, inflammation etc.).

HSPs participate in the correct folding, activity, transport and stability of proteins. HSPs have intra-(cytoprotective) and extracellular (danger signal) functions. However, they also prevent cell death, for instance by preventing post-mitochondrial apoptosis in caspase-dependent (e.g., HSP27, HSP70, and HSP90) and/or independent (e.g., HSP70) pathways (Gallucci and Matzinger, Curr Opin Immunol 2001 February; 13(1):114-9). Many cancers, such as melanomas, colorectal cancers, prostate cancer, breast and lung, are characterized by overexpression of HSPs (Bauer et al., Cellular oncology 35:197-205. 2012; Huang et al., 2005 Journal of Huazhong University of Science and Technology, Yixue Yingdewen ban 25:693-695; Katsogiannou et al., 2015, Cancer treatment reviews 41:588-597), associated with a bad prognosis for patients (Storm et al., 1996, Annals of surgical oncology 3:570-573). In particular, HSP110 comprises four members named HSP110 protein, APG-1, APG-2 and GRP170. The HSP110 protein is represented by two proteins alpha and beta, described for example in Berthenet et al 2015 (Médecine humaine et pathologie, Université de Bourgogne, NNT: 2015DIJOS059, https://tel.archives-ouvertes.fr/tel-01289793).

Like other stress inducible HSPs, HSP110 protein, also named HSP105, protects the cell against adverse conditions and is one of the most expressed in several cellular type in the mammal. However, HSP110 protein plays a role in the anti-aggregating and anti-apoptosis functions. Recently, it has been demonstrated that HSP110 protein accumulates abnormally in cancer cells and this is believed to enhance their survival (Yamagishi et al., The FEBS journal 275 (18), 4558 (2008); Hosaka et al., Cancer science 97 (7), 623 (2006); Yamagishi et al, Experimental cell research 312 (17), 3215 (2006); Siatskas et al., Faseb J 19 (12), 1752 (2005)). Moreover, HSP110 protein also has an effect in macrophages polarization: it favors the formation of macrophages with a pro-inflammatory phenotype thereby facilitating tumor progression (Berthenet et al 2015, Médecine humaine et pathologie, Université de Bourgogne, NNT: 2015DIJOS059, https://tel.archives-ouvertes.fr/tel-01289793). HSP110 protein is especially strongly expressed in colon cancer cells (Kai et al, Oncology reports 10 (6), 1777 (2003)).

Involvement of HSPs in multiple tumorigenic processes let to development of inhibitors of these proteins.

For example, geldanamycin derivatives, called 17AAG, has been developed to inhibit the HSP90 activity (Roh et al. 2013, Cell death & disease 4: e956; Ye et al. 2015, Journal of cellular and molecular medicine 19:651-663). Other compounds target the HSP70 activity and play a role on the cellular death (Steele. et al 2009, Blood 114:1217-1225; Berthen et al 2015, Médecine humaine et pathologie, Université de Bourgogne, NNT: 2015DIJOS059, https://tel.archives-ouvertes.fr/tel-01289793).

Recently it has been demonstrated that HSP110 protein enhances certain signaling pathways and transcription factors, notably the proliferative Wnt/β-Catenin pathway and in particular the transcription factor STAT3 (Signal Transducer and Activator of Transcription 3) (Olszak et al., 2014 Nature 509, 497-502 (2014); Yu, N. et al. 2015 Molecular and cellular biology 35:1390-1400). For example, HSP110 protein induces the phosphorylation of STAT3 protein by the IL-6 pathways and its migration to the nucleus. Especially, in the IL-6 pathways, the phosphorylation of STAT3 protein is provoked by JAK2, and induced by the binding of HSP110 protein at the amino acid tyrosine 705 of STAT3 protein. STAT3 protein therefore activates gene implicated in cellular survival.

STAT3 protein is active in lot of human cancers and responsible for serious outcomes (Morikawa et al, Clin Cancer Res 2011; Huang et al Oncogene, Oncogene 2016 Feb. 11; 35(6):783-92). As a consequence, the development of inhibitors of STAT3 protein remains an active area of research. However, STAT3 protein is an essential transcriptional factor for many cellular functions and its inhibition can cause adverse effects (Welte et al PNAS Feb. 18, 2003. 100 (4) 1879-1884; Mantel et al, blood 2012 Sep. 27; 120(13):2589-99).

For these reasons, there remains a need for compounds for use for treating cancer, especially cancer induced by an HSP110 activity.

SUMMARY OF THE DISCLOSURE

The invention relates to a compound of formula (I):

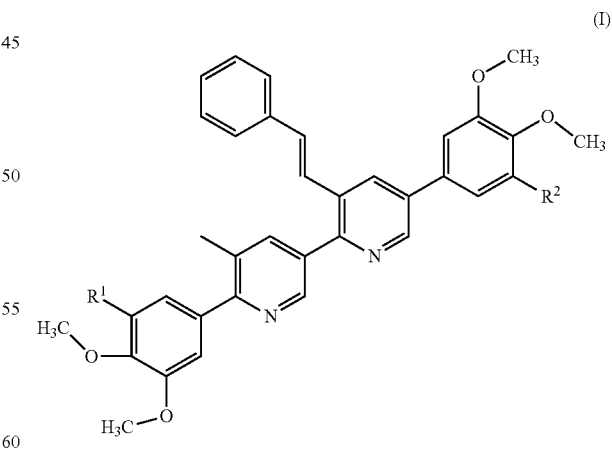

wherein:
R$^1$ and R$^2$ represent independently a group selected among H and a (C1-C3) alkoxy group;
or one of its pharmaceutically acceptable salts and/or racemic, enantiomeric, diastereoisomeric or tautomeric forms;
for use in the treatment of a HSP110-associated cancer.

The present invention also relates to a method for determining the responsiveness of a cancer patient to a HSP110 inhibitor comprising at least the steps of:
- a) determining in a sample previously collected from the said patient the ability of said patient to express a functional HSP110 protein, and
- b) selecting the said patient as responsive to a cancer treatment with a HSP110 inhibitor when said HSP110 protein is functional.

In particular, the invention also relates to a method for determining the responsiveness of a cancer patient to a HSP110 inhibitor comprising at least the steps of:
- a) determining, in a nucleic acid-containing sample previously collected from the said patient, the sequence of the HSP110-encoding nucleic acid, and
- b) selecting the said patient as responsive to a cancer treatment with a HSP110 inhibitor when the sequence determined at step a) encodes a HSP110 protein or variant thereof that is functional for phosphorylating STAT3 protein.

The present invention also pertains to a method for determining responsiveness of a cancer patient to a HSP110 inhibitor comprising a step of determining phosphorylation of STAT3 in sample, in particular a tumor tissue sample, that has been previously collected from the said cancer patient.

The present invention also relates to a method for treating an individual affected with a HSP110-associated cancer comprising the steps of:
- a) determining the responsiveness of a cancer patient to a HSP110 inhibitor comprising at least the steps of:
  - a1) determining, in a sample previously collected from the said patient, the ability of said patient to express a functional HSP110 protein;
  - a2) selecting the said patient as responsive to a cancer treatment with a HSP110 inhibitor when said HSP110 protein is functional, and
- b) administering an anti-cancer treatment to the said patient when selected as responsive to a cancer treatment with a HSP110 inhibitor at step a2).

In particular, the invention also relates to a method for treating an individual affected with a HSP110-associated cancer comprising the steps of:
- a) determining the responsiveness of a cancer patient to a HSP110 inhibitor comprising at least the steps of:
  - a1) determining, in a nucleic acid-containing sample previously collected from the said patient, the sequence of the HSP110-encoding nucleic acid;
  - a2) selecting the said patient as responsive to a cancer treatment with a HSP110 inhibitor when the sequence determined at step a) encodes a HSP110 protein or variant thereof that is functional for phosphorylating STAT3, and
- b) administering an anti-cancer treatment to the said patient when selected as responsive to a cancer treatment with a HSP110 inhibitor at step a2).

This invention also concerns a method for treating an individual affected with a HSP110-associated cancer comprising a step of administering to the said individual a HSP110 inhibitor as described herein, and especially a HSP110 inhibitor of Formula (I).

This invention further relates to a HSP110 inhibitor, and especially a HSP110 inhibitor of Formula (I), for use in the treatment of a HSP110-associated cancer.

This invention also concerns the use of a HSP110 inhibitor, and especially a HSP110 inhibitor of Formula (I), for preparing a medicament for treating a HSP110-associated cancer.

This invention also pertains to a method for treating an individual affected with a HSP110-associated cancer comprising the steps of:
- a) determining the responsiveness of a cancer patient to a HSP110 inhibitor comprising at least the steps of:
  - a1) preparing a cell lysate from the tumor tissue previously collected from the said cancer patient;
  - a2) detecting phosphorylated STAT3 protein in the said cell lysate, e.g. by using antibodies binding specifically to phosphorylated STAT3 protein,
  - a3) selecting the said patient as responsive to a cancer treatment with a HSP110 inhibitor when phosphorylated STAT3 is detected at step a2), and
- b) administering an anti-cancer treatment to the said patient when selected as responsive to a cancer treatment with a HSP110 inhibitor at step a3).

The compounds according to the present invention were described in WO2015/132727, for treating ovarian cancer as Mcl-1 modulating compounds. Nonetheless the surprising use of the compound of formula (I), for use in the treatment of a HSP110-associated cancer was never illustrated before this work.

DESCRIPTION OF THE FIGURES

FIG. 2.

FIG. 3:

FIG. 4:

FIG. 5:

FIG. 6: In vivo reduction of tumor volume (in $mm^3$) per days (Scale bar 500 $mm^3$ and 2 days). Mean volume+-SD (standard deviation) is represented (n=6—six mice per group) (Statistical analysis has been performed by ANOVA ($p<0.05$).

FIG. 7:

FIG. 8:

FIG. 9:

Figure 10A:
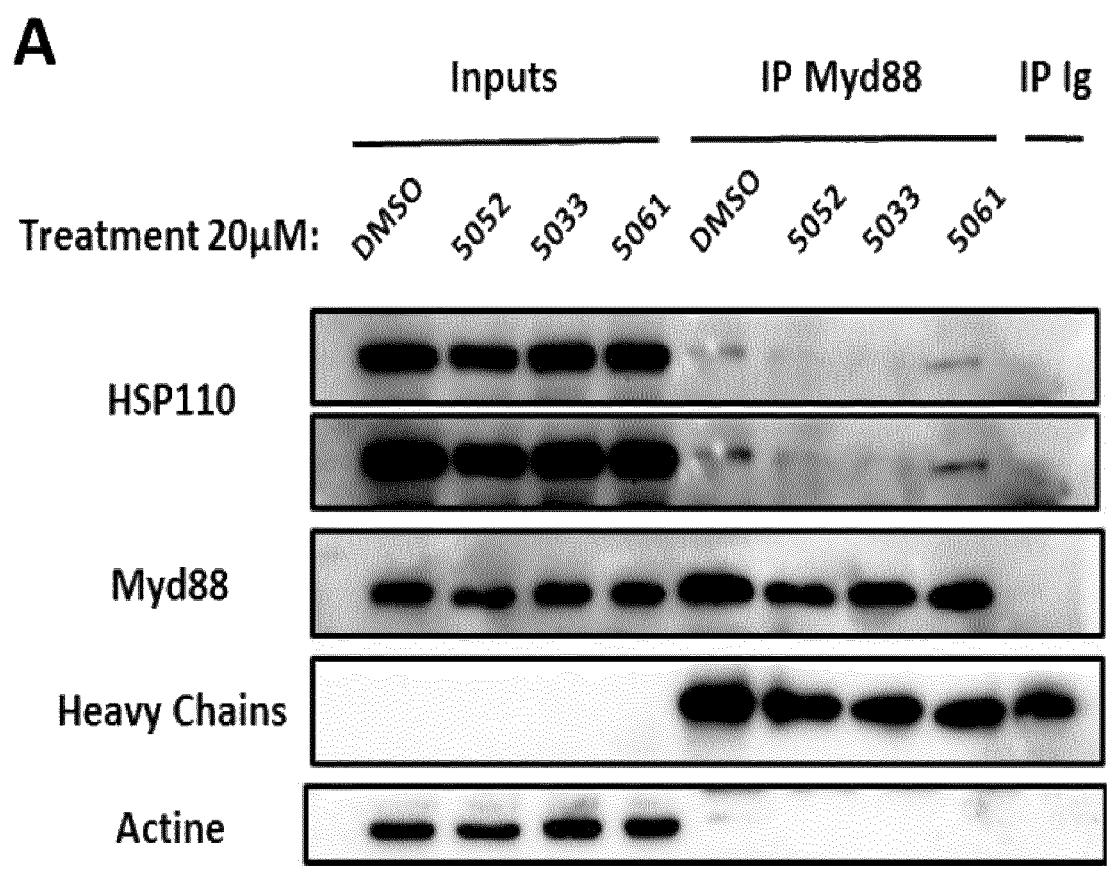
FIG. 10A: Immunoprecipitation (IP) analysis of HSP110 (first line), Myd88 (second line), heavy chains (third line) and actin (fourth line) in large B cell lymphoma cell lines (DLBCL).

Left part of FIG. 10A ("Inputs"): treated with (from left to right column of the left part of FIG. 10A) DMSO, compound 52 (5052), compound 33 (5033) and compound 61 (5061) (Negative control);

Middle part of FIG. 10A ("IP Myd88"): treated with (from left to right column of the middle part of FIG. 10A) DMSO, compound 52, compound 33 and compound 61 (as the negative control); Myd88 was immunoprecipitated with an antibody specifically directed against Myd88.

Right part of FIG. 10A: incubation with "IP Ig"; An immunoprecipitation was performed with an irrelevant antibody that forms a negative control, so as to show that what is detected in the immunoprecipitate is an association to the protein and not to the antibody.

Figure 10B:
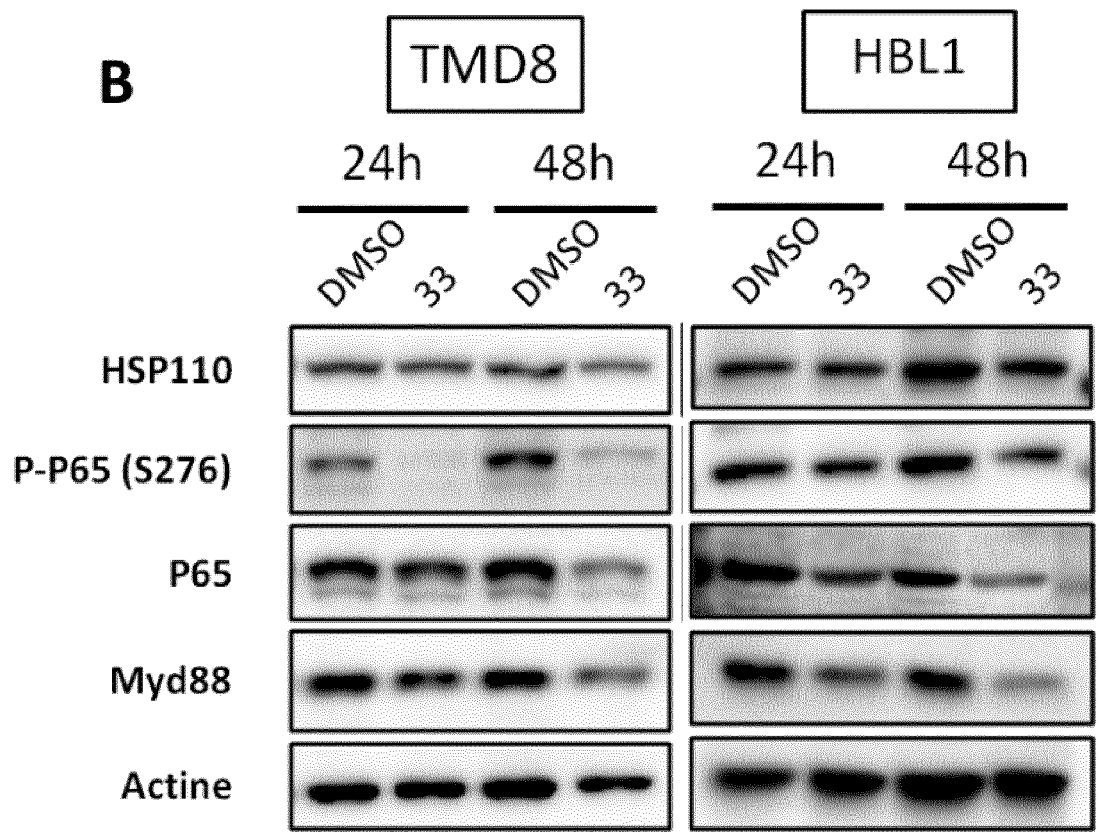
FIG. 10.

FIG. 10B: Expression of HSP110 (first line), P-P65 (S276) (second line), P65 (third line), Myd88 (fourth line) and Actin (fifth line) in TMD8 human B cell lymphoma cell line (left part of FIG. 10B) or in HBL1 human diffuse large B-cell lymphoma cell line (right part of FIG. 10B), both cell lines being treated with Control (DMSO) and compound 33.

Figure 10C:
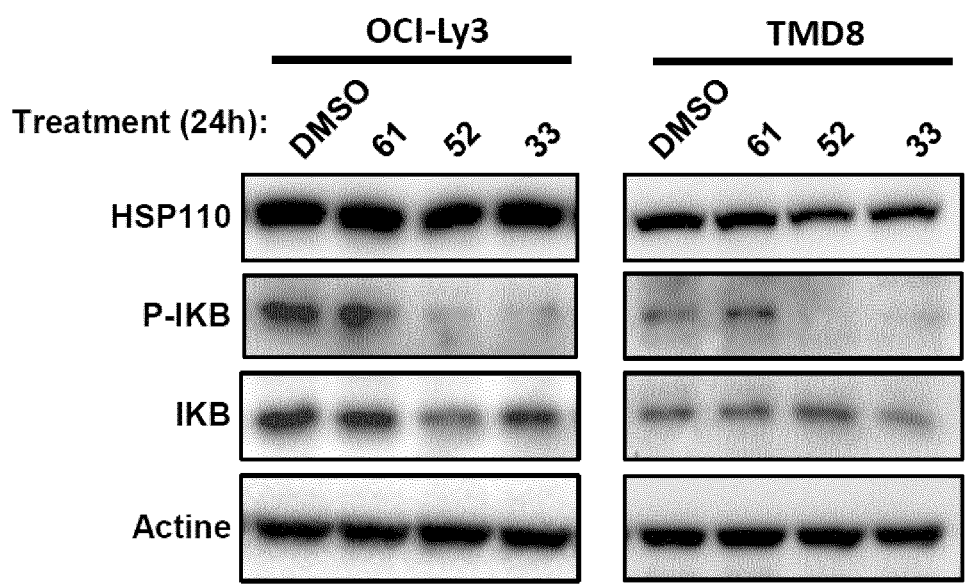

FIG. 10C: Expression, after 24 h of treatment, of HSP110 (first line), P-IKB (second line), IKB (third line) and Actin (fourth line) in TMD8 human B cell lymphoma cell line (right part of FIG. 10C) or in OCI-Ly3 human diffuse large B-cell lymphoma cell line (left part of FIG. 10C), both cell lines being treated with Control (DMSO), control compound 61, compound 52 and compound 33.

Figure 10D:
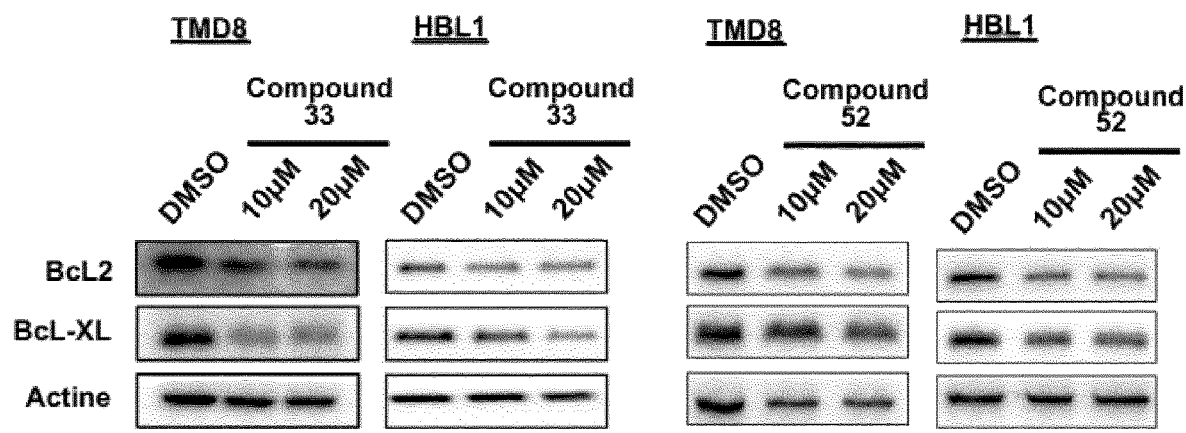

FIG. 10D: Expression analysis of BcL2 (first line), BcL-XL (second line), and Actin (third line) in TMD8 human B cell lymphoma cell line or in HBL1 human diffuse large B-cell lymphoma cell line, both cell lines being treated with Control (DMSO), compound 33 and compound 52.

Figure 10E:
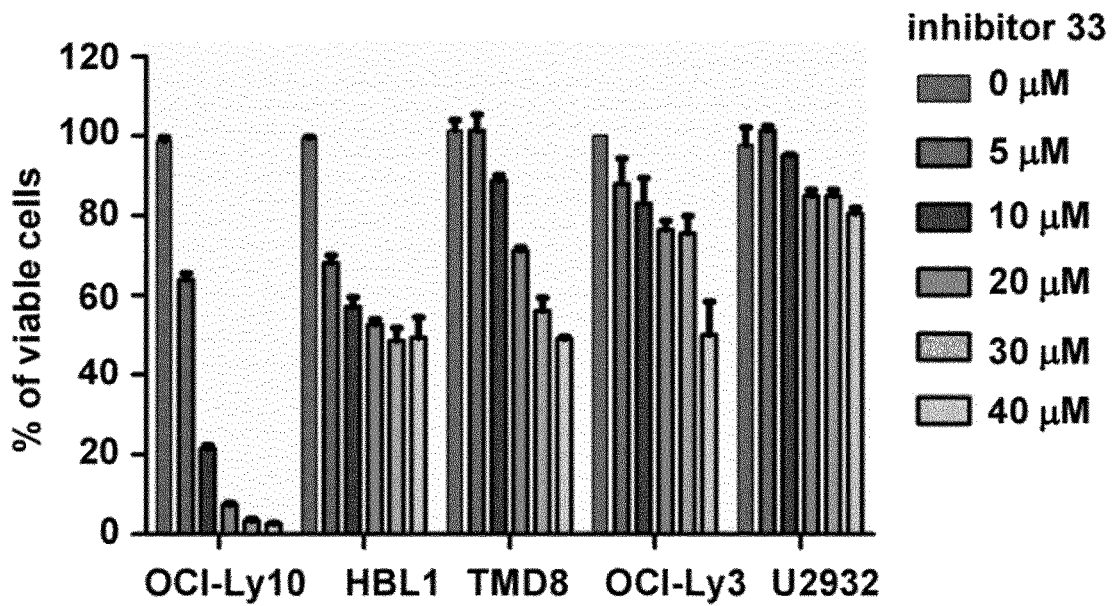

FIG. 10E: Viability of various B-cell lymphoma cell lines treated with increasing concentrations of compound 33 (inhibitor 33).

Groups of bars, from the left to the right of FIG. 10E: (i) OCI-Ly10 human diffuse large B-cell lymphoma cell line, (ii) HBL1 human diffuse large B-cell lymphoma cell line, (iii) TMD8 human B cell lymphoma cell line, (iv) OCI-Ly3 human large B-cell lymphoma cell line and (v) U2932 human diffuse large B-cell lymphoma cell line.

In each group of bars, from the left to the right: (i) Control, without treatment, (ii) Compound 33 at 5 µM, (iii) Compound 33 at 10 µM, (iv) Compound 33 at 20 µM, (v) Compound 33 at 30 µM, (vi) Compound 33 at 40 µM.

Ordinate axis: percent of viable cells

Figure 10F:
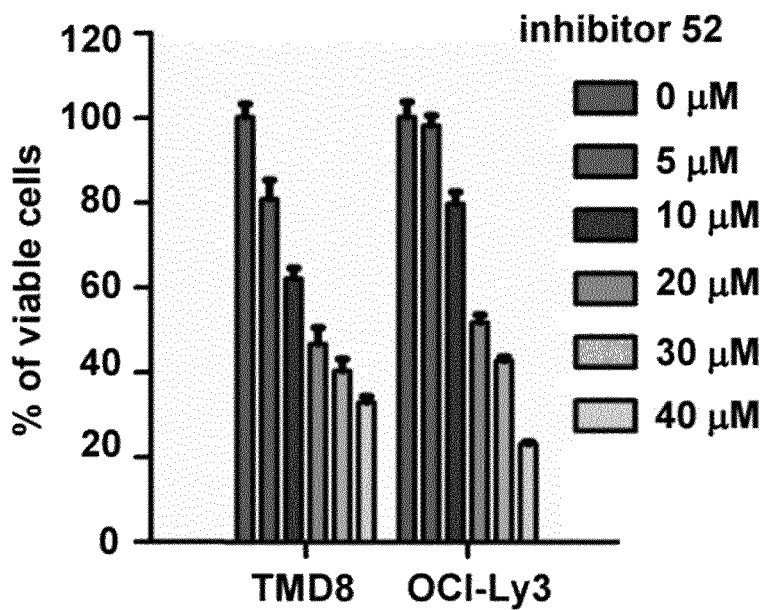

FIG. 10F: Viability of various B-cell lymphoma cell lines treated with increasing concentrations of compound 52 (inhibitor 52).

Groups of bars, from the left to the right of FIG. 10F: (i) TMD8 human B cell lymphoma cell line and (ii) OCI-Ly3 human large B-cell lymphoma cell line.

In each group of bars, from the left to the right: (i) Control, without treatment (0 µM), (ii) Compound 52 at 5 µM, (iii) Compound 52 at 10 µM, (iv) Compound 52 at 20 µM, (v) Compound 52 at 30 µM, (vi) Compound 52 at 40 µM.

Ordinate axis: percent of viable cells

Figure 11A:
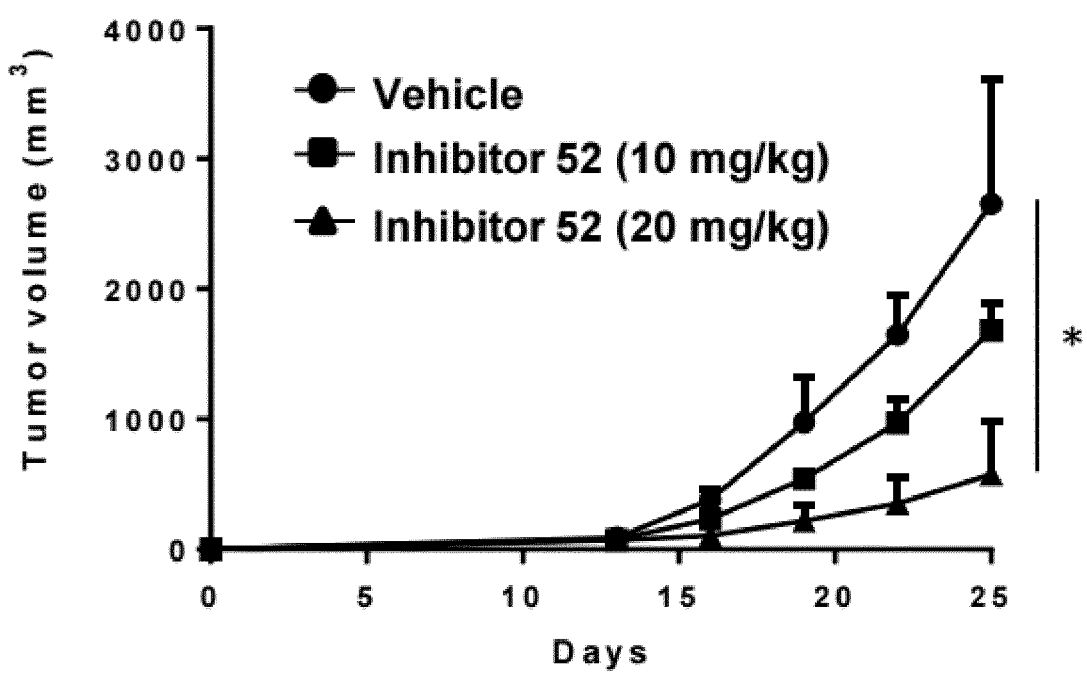

FIG. 11:

FIG. 11A: Tumor volume monitoring of TMD8 human DLBCL cells grown in Immunodeficient mice treated intraperitoneally with the compound 52 (=inhibitor 52) at 10 or 20 mg/kg or with vehicle at the same frequency. (Abscissa: Days from 0 to 25 in day; Ordinate: Tumor volume in $mm^3$ from 0 to 4000 (scale 1000)).

Figure 11B:
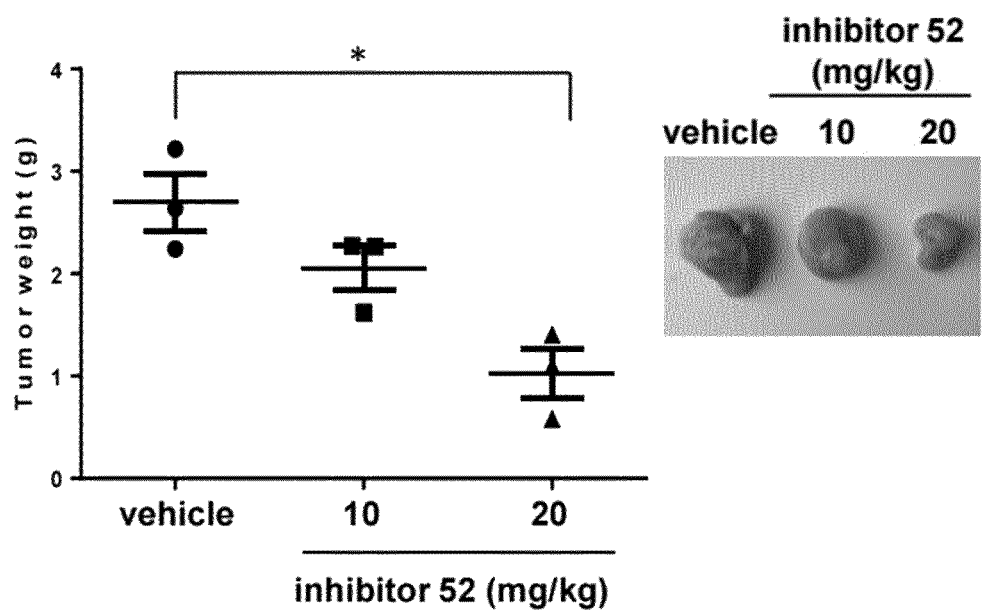

FIG. 11B: Tumor weight monitoring of TMD8 human DLBCL cells grown in Immunodeficient mice treated intraperitoneally with the compound 52 (=inhibitor 52) at 10 or 20 mg/kg or with vehicle at the same frequency. (Abscissa: Treatments vehicle, 10 mg/kg or 20 mg/kg of compound 52; Ordinate: Tumor weight in g from 0 to 4 g (scale 1)).

Figure 11C:
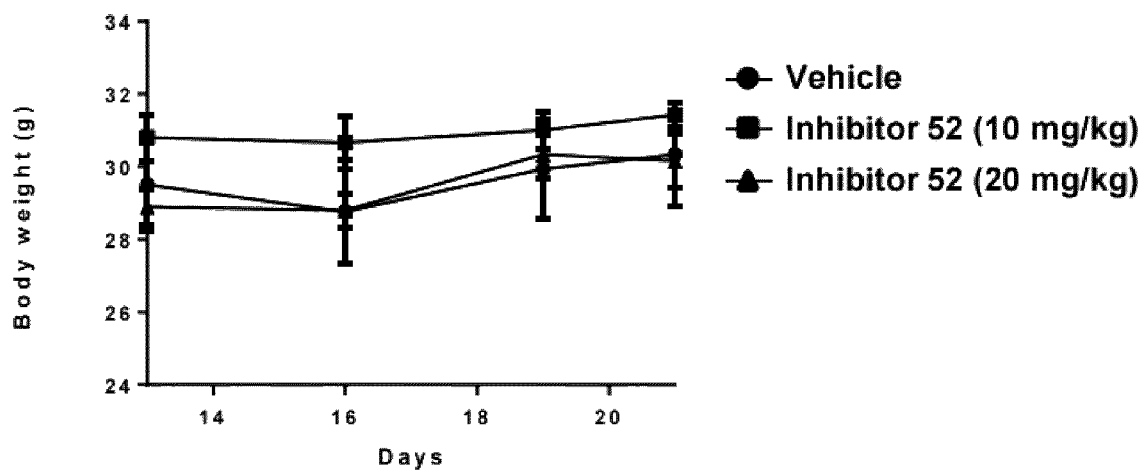

FIG. 11C: Body weight monitoring of Immunodeficient mice treated intraperitoneally with the compound 52 (=inhibitor 52) at 10 or 20 mg/kg or with vehicle at the same frequency. (Abscissa: Days from 0 to 20 in day; Ordinate: Body weight in g from 24 to 34 g (scale 2)).

Figure 11D:
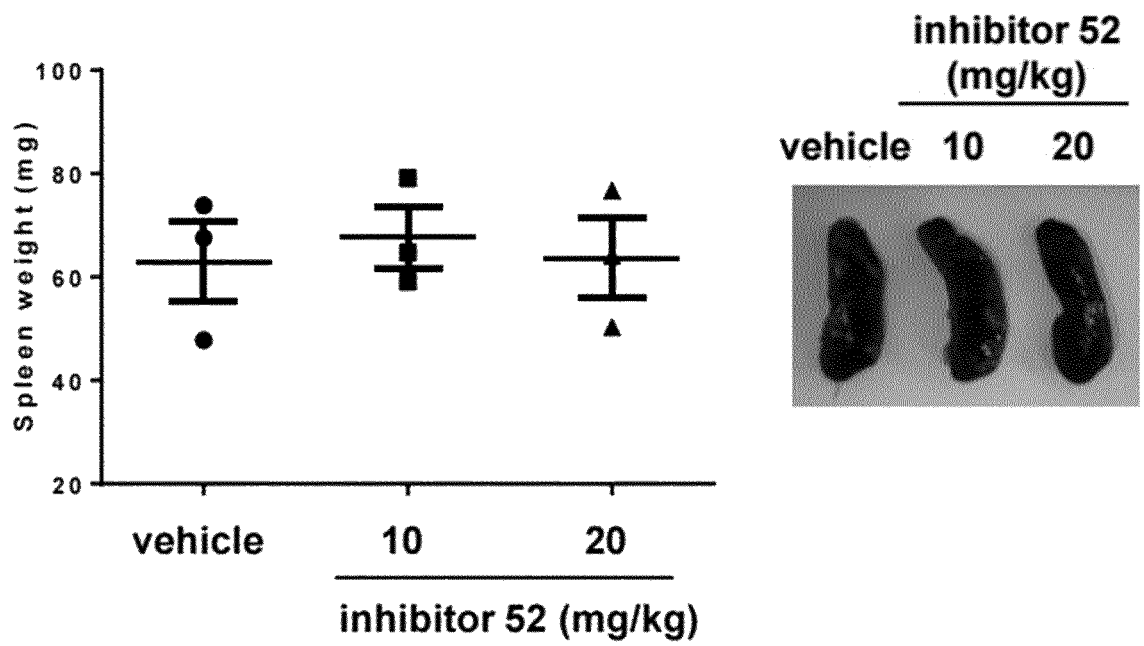

FIG. 11D: Spleen weights monitoring of Immunodeficient mice treated intraperitoneally with the compound 52 (=inhibitor 52) at 10 or 20 mg/kg or with vehicle at the same frequency. (Abscissa: Treatments vehicle, 10 mg/kg or 20 mg/kg of compound 52; Ordinate: Spleen weight in mg from 20 to 100 mg (scale 20)).

Figure 12:
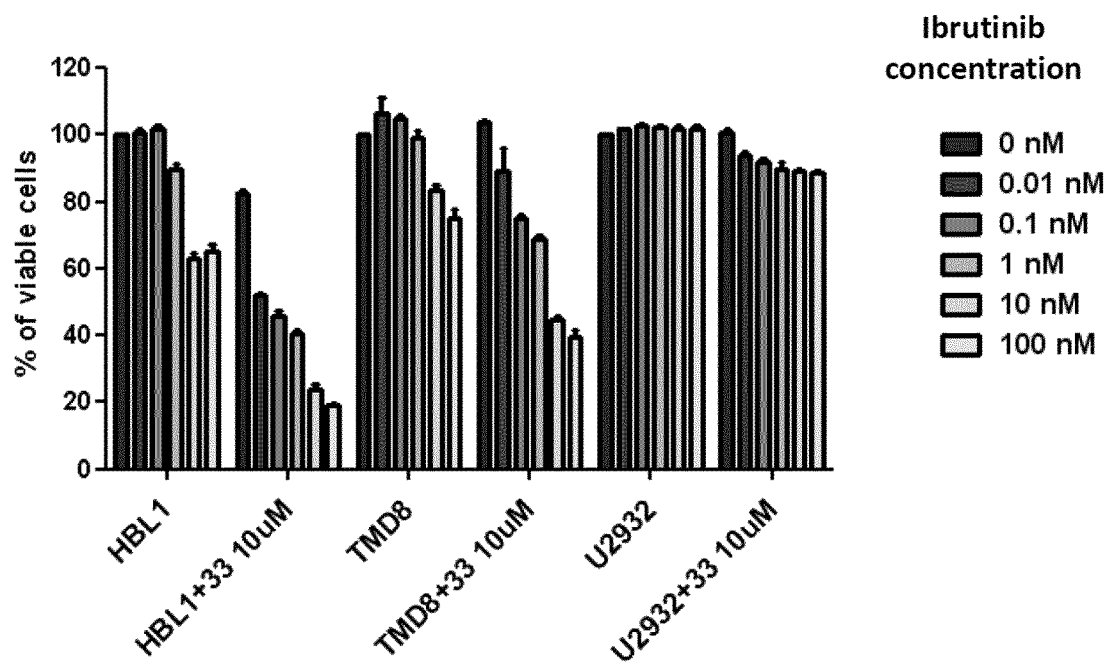

FIG. 12: Viability of various B-cell lymphoma cell lines treated with a suboptimal concentration of compound 33 (i) alone or (ii) in combination with increasing concentrations of Ibrutinib.

Groups of bars, from the left to the right of FIG. 12: (i) HBL1 human diffuse large B-cell lymphoma cell line not treated with compound 33 and treated with and increasing concentrations of Ibrutinib, (ii) HBL1 human diffuse large B-cell lymphoma cell line treated with 10 µM of compound 33 and increasing concentrations of Ibrutinib, (iii) TMD8 human B cell lymphoma cell line not treated with compound 33 and treated with and increasing concentrations of Ibrutinib, (iv) TMD8 human B cell lymphoma cell line treated with 10 µM of compound 33 and increasing concentrations of Ibrutinib, (v) U2932 human diffuse large B-cell lymphoma cell line not treated with compound 33 and treated with and increasing concentrations of Ibrutinib, and (vi). U2932 human diffuse large B-cell lymphoma cell line treated with 10 µM of compound 33 and increasing concentrations of Ibrutinib.

In each group of bars, form the left to the right: (i) Control (0 nM), without treatment with Ibrutinib, (ii) Ibrutinib at 0.01 nM, (iii) Ibrutinib at 0.1 nM, (iv) Ibrutinib at 1 nM, (v) Ibrutinib at 10 nM, (vi) Ibrutinib at 100 nM.

Ordinate axis: percent of viable cells

DETAILED DESCRIPTION OF THE INVENTION

The inventors have unexpectedly shown herein that a compound of formula (I) reduces cancer tumor in HSP110-related cancer. As disclosed in the examples herein, a compound of formula (I), when used in vitro, targets HSP110 protein, at least blocks the phosphorylation of STAT-3 or MyD88 stability and in most cases blocks the anti-aggregation function of HSP110. Further, a compound of formula (I) allows in vivo the diminution of the tumor volume and the polarization of macrophages, which prevent the cancer evolution. Still further, the inventors have shown the anti-cancer activity of a compound of formula (I) against a plurality of HSP110-related cancers. Additionally, it has been shown that a compound of formula (I) acts synergistically with other anti-cancer agents, and induces a potentialization of the effect of other anti-cancer agents.

Compound

As above identified, the compound used according to the invention correspond to formula (I):

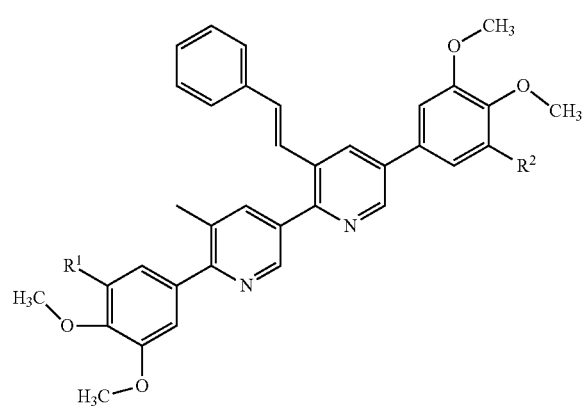

(I)

wherein:
$R^1$ and $R^2$ represent independently a group selected among H and a (C1-C3) alkoxy group;
or one of its pharmaceutically acceptable salts and/or racemic, enantiomeric, diastereoisomeric or tautomeric forms; for use in the treatment of a HSP110-associated cancer.

In some embodiments, the compound used according to the invention consists of a compound of formula (I), wherein $R^1$ is selected from a group consisting of H and a (C1-C3) alkoxy group and $R^2$ is a (C1) alkoxy group.

In some preferred embodiments, the compound used according to the invention consists of a compound of formula (I), wherein $R^1$ is selected from a group consisting of H or a (C1) alkoxy group and $R^2$ is a (C1) alkoxy group; or one of its pharmaceutically acceptable salts and/or racemic, enantiomeric, diastereoisomeric or tautomeric forms.

In some specific embodiments of a compound of formula (I), R1 and $R^2$ are both a H.

In some other specific embodiments of a compound of formula (I), $R^1$ and $R^2$ are both a (C1-C3) alkoxy group, preferably a (C1) alkoxy group. In another particular embodiment of a compound of formula (I), $R^1$ is a H and $R^2$ is (C1-C3) alkoxy group, preferably a (C1) alkoxy group.

It may be noticed that the compounds of the invention may contain one or several asymmetric carbon atoms. Accordingly, they may exist in the form of enantiomers or diastereoisomers. These enantiomers and diastereoisomers, and also mixtures thereof, including racemic mixtures, form part of the invention. Further, the alkene functions present in the compound of the invention can either be in the Z or in the E configuration.

The present invention also relates to the tautomeric forms of the compounds according to the invention. The term "a tautomeric form" is understood to mean a constitutional isomer, the structure of which differs in the position of an atom, for example a hydrogen atom, and of one or more multiple bonds. Two tautomeric forms are capable of easily and reversibly converting into one another.

The compounds of the invention may also exist in the form of bases or of acid-addition salts. These salts are pharmaceutically acceptable acids and also form part of the invention.

The term "pharmaceutically acceptable" means what is useful in preparing a pharmaceutical composition generally safe, non-toxic, and neither biologically nor otherwise undesirable and includes what is acceptable for veterinary as well as human pharmaceutical use.

In addition to pharmaceutically-acceptable salts, other salts are included in the invention. They may serve as intermediates in the purification of the compounds, in the preparation of other salts, or in the identification and characterization of the compounds or intermediates.

The compounds of the invention may also exist in the form of hydrates or solvates, i.e. in the form of associations or combinations with one or more molecules of water or with a solvent such as methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

In the context of the present invention, a (C1-C3) alkoxy group is a radical —O-alkyl in which the alkyl group is a linear or branched saturated aliphatic group, comprising from 1 to 3 carbon atoms. Examples of alkyl group that may be mentioned include methyl, ethyl, n-propyl, isopropyl. In particular, the (C1-C3) alkoxy group may be a methoxy group, also named (C1) alkoxy group.

In particular, compounds according to the invention may also correspond to the compound of formula (II), (III) and (IV), as described in table 1:

TABLE 1

Formula (II) (also named compound 33)

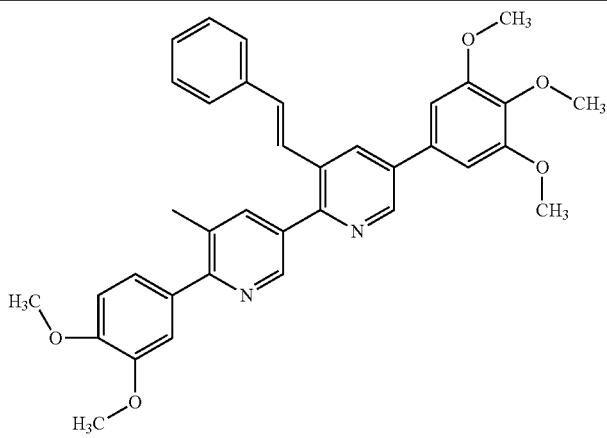

Formula (III) (also named compound 52)

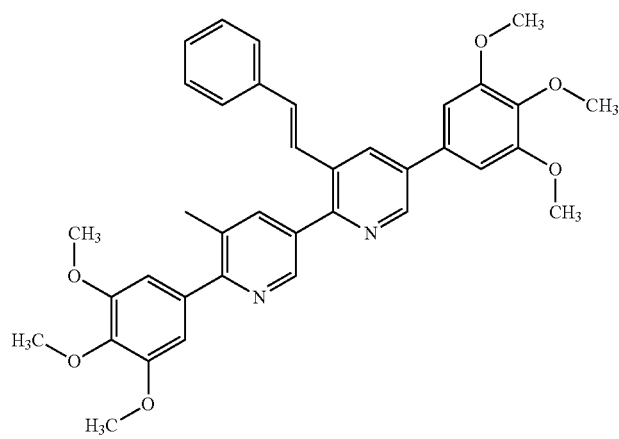

Formula (IV) (also named compound 51)

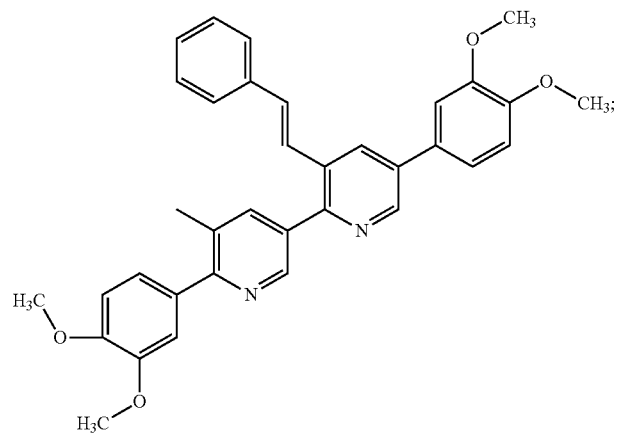

or one of its pharmaceutically acceptable salts and/or racemic, enantiomeric, diastereoisomeric or tautomeric forms.

In another particular embodiment, a compound of the present invention corresponds to (E)-6'-(3,4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine (formula (III)), (E)-5,6'-Bis(3,4-dimethoxyphenyl)-5'-methyl-3-styryl-2,3'-bipyridine (formula (IV)) and their mixtures, or one of their pharmaceutically acceptable salts and/or racemic, enantiomeric, diastereoisomeric or tautomeric forms.

The compounds of formula (I), in particular compounds of formula (II), (III) and (IV) according to the present invention may be prepared by adaptation of known methods and especially by methods described in document number WO2015132727 or "Gloaguen et al. 2015, Journal of Medicial Chemistry (DOI: 10.1021/jm500672y).

Therapeutic Use

As previously specified, the present invention relates to a HSP110 inhibitor, and especially a compound of formula (I) for use in the treatment of a HSP110-associated cancer. In other words, the present invention describes the use of a HSP110 inhibitor, and especially a compound of formula (I) as described herein to treat HSP110-associated cancer.

In yet other words, the present invention describes the use of a compound of formula (I) as described herein for the preparation of a medicament intended to treat an HSP110-associated cancer.

As used herein, an HSP110-associated cancer is a cancer for which tumor cell proliferation and/or the absence of tumor cell death is correlated with the activity of HSP110 protein. In particular, an HSP110-associated cancer encompasses cancers wherein HSP110 protein is functional for STAT3 phosphorylation (P-STAT3), and/or wherein HSP110 protein maintains his anti-aggregation activity, and/or wherein HSP110 protein negatively affects the anticancer immune response.

In particular, a cancer wherein HSP110 protein is functional for P-STAT3 is a cancer for which the HSP110 protein or variant thereof produced in the cancer patient's body has the ability to phosphorylate human STAT3 protein.

In particular, a cancer wherein HSP110 protein maintains his anti-aggregation activity is a cancer for which the HSP110 protein or variant thereof produced in the cancer patient's body has the ability to maintain his chaperone activity with respect to the anti-aggregation activity.

The anti-aggregation activity of the HSP110 protein corresponds to the chaperone activity of HSP110 protein which activity consists of blocking the folding and/or stability of proteins in particular in cancer condition.

In particular, a cancer wherein HSP110 protein negatively affects the anticancer immune response is a cancer for which the HSP110 protein or variant thereof produced in the cancer patient's body has the ability to induce polarization of macrophages, preferably the HSP110 protein has the ability to induce polarization of pro inflammatory macrophages with profile M2.

As regards the human STAT3 protein, it may for example be referred to the amino acid sequence disclosed in the UniProt sequence database under the reference number P40763. Regarding a STAT3-encoding nucleic acid, it may be referred to the nucleic acid described in the HGCN database under the reference number 11364 (Gene ID 6774).

As regards the human HSP110 protein, it may for example be referred to the amino acid sequence disclosed in the UniProt sequence database under the reference number Q92598. Regarding a HSP110-encoding nucleic acid, it may be referred to the nucleic acid described in the HGCN database under the name HSPH1 and the reference number 16969. In particular the human HSP110 protein corresponds to SEQ ID NO: 1.

In one embodiment, HSP110-associated cancer consists of a cancer wherein the HSP110 protein is devoid of a HSP110 loss-of-function mutation preventing STAT3 phosphorylation.

In another embodiment, HSP110-associated cancer consists of a cancer wherein the cancer tumor expresses a HSP110 protein that is devoid of one or more mutations in the nucleotide binding domain of HSP110 protein. In particular HSP110-associated cancer consists of a cancer wherein the HSP110 protein is devoid of one or more mutations at the fixation site of the HSP110 protein.

In another particular embodiment, HSP110-associated cancer consists of a cancer wherein the cancer tumor expresses a HSP110 protein that is devoid of one or more mutations in the nucleotide binding domain of HSP110 protein, wherein the said one or more mutations prevent HSP110 to phosphorylate STAT3 protein. In a more particular embodiment HSP110-associated cancer consists of a cancer wherein the HSP110 protein is devoid of one or more mutations at the fixation site of the HSP110 protein, wherein the said one or more mutations prevent HSP110 to phosphorylate STAT3 protein.

The nucleotide-binding domain is represented by the ATP binding domain of HSP110 protein and is defined as by the amino acid sequence starting at the amino acid located at position 1 and ending at the amino acid located at position 378 of SEQ ID NO:1, the said nucleotide-binding domain being represented by SEQ ID NO: 2.

The fixation site of the HSP110 protein is represented by the interaction region between the nucleotide-binding domain of HSP110 protein and STAT3 protein, which interaction region is a conformational region and comprises preferably the amino acids 184 to 193 of SEQ ID NO. 1 (SEQ ID NO: 3), the amino acids 275 to 284 of SEQ ID NO. 1 (SEQ ID NO: 4), the amino acids 341 to 355 of SEQ ID NO. 1 (SEQ ID NO: 5), and/or the amino acids 360 to 364 of SEQ ID NO. 1 (SEQ ID NO: 6).

HSP110-associated cancer encompasses a cancer for which tumor cell proliferation and/or the absence of tumor cell death is correlated with the activity of HSP110 protein and wherein HSP110 interacts with MyD88. As shown herein, a compound of Formula (I) is able to alter the interaction between HSP110 and MyD88, which induces a degradation of the oncogene MyD88. By MyD88 (for "Myeloid differentiation primary response 88"), it is intended herein the human protein having 296 amino acids in length and which is of the amino acid sequence that is referred to the Accession number AAC50954.1 in the GenBank sequence database.

Further, HSP110-associated cancer encompasses DLBCL (for "Diffuse Large B-Cell Lymphoma") which is an aggressive lymphoproliferative disorder wherein HSP110 interacts with Myd88. Several mutations in the B-cell receptor and the MyD88 signaling pathway components, such as MyD88 L265P, are implicated in this aberrant activation. HSP110 is a regulator of NF-κB signaling through MyD88 L265P binding and stabilization in DLBCL (Boudesco et al, *Blood* 2018 Aug. 2; 132(5):510-520). Furthermore, shRNA-mediated HSP110 silencing decreased the survival of several DLBCL cell lines in vitro. It is worth mentioning that HSP110 did not have any effect in U2932 cells, which in contrast to the other cell lines analyzed, do not bear MyD88 and CBM mutations. In DLBCL patients, HSP110 expression was higher in lymph-node biopsies than in normal reactive lymph nodes and a strong correlation was found between the level of HSP110 and MyD88.

According to the invention, a compound of formula (I) for use in the treatment of a HSP110-associated cancer is a compound which inhibits phosphorylation of STAT3 protein by interacting with HSP110 protein, in particular by interacting with the nucleotide-binding domain of HSP110 protein, more particularly by interacting with the fixation site of the HSP110 protein.

In some embodiments, the HSP110-associated cancer is a colon or colorectal cancer, especially in human.

In some other embodiments, the HSP110-associated cancer is a lymphoma, which includes a B-cell lymphoma, such as a diffuse large B cell lymphoma (DLBCL), especially in human.

An illustrative method for determining the ability of a HSP110 protein or variant thereof to phosphorylate human STAT3 protein is disclosed in the examples herein.

In some embodiments, a method for determining the ability of a HSP110 protein or variant thereof to phosphorylate human STAT3 protein comprises the steps of:

a) preparing a cell lysate from the tumor tissue previously collected from the said cancer patient;
b) detecting phosphorylated STAT3 protein in the said cell lysate, e.g. by using antibodies binding specifically to phosphorylated STAT3 protein.

In some embodiments, step b) may be performed by immunoblotting by using antibodies binding specifically to phosphorylated STAT3 protein, as it is disclosed in the examples herein.

Antibodies directed against phosphorylated STAT3 protein that may be used for performing the above method include the anti-phosphorylated-STAT3 (Tyr705) antibodies available under the reference numbers #44-308G, #710093, #701062 and #12-9033-42 (ThermoFisher Scientific).

In some embodiments of the method, e.g. in some embodiments of step b), it is also ensured that the cells also produce HSP110 protein or a variant thereof. Detection of HSP110 protein or a variant thereof may be performed by PCR or by immunoblotting by using antibodies binding to HSP110 or a variant thereof.

As regards the human HSP110 protein, it may for example be referred to the amino acid sequence disclosed in the UniProt sequence database under the reference number Q92598. Regarding a HSP110-encoding nucleic acid, it may be referred to the nucleic acid described in the HGCN database under the name HSPH1 and the reference number 16969. In particular the human HSP110 protein corresponds to SEQ ID NO: 1.

Illustratively; it may be used the anti-HSP110 antibodies available under the reference number ABIN4320617 (Antibodies-online.com), the anti-HSP110 antibody available under the reference number ASI-SPA-1101-E (Enzo) or also the anti-HSP110 antibodies available under the reference numbers ab24503, ab109624, ab108625, ab24503 (Abcam).

For example, the HSP110-associated cancer is selected from the group consisting of the colorectal cancer, stomach cancer, endometrial cancer, bladder cancer, urinary tract cancer, ovary cancer, prostate cancer, lymphomas, leukemia, glioblastoma, astrocytoma and neuroblastoma, and preferably colorectal cancer, stomach cancer, endometrial cancer, more preferably colorectal cancer.

In one embodiment, the HSP110-associated cancer is selected from the group consisting of the colorectal cancer, stomach cancer, endometrial cancer, bladder cancer, urinary tract cancer, ovary cancer, prostate cancer, lymphomas, leukemia, glioblastoma, astrocytoma and neuroblastoma, and preferably colorectal cancer, lymphomas, stomach cancer, endometrial cancer, more preferably colorectal cancer and lymphomas.

Another subject of the invention is the use of (E)-6'-(3, 4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine (formula (III)), (E)-5,6'-Bis(3,4-dimethoxyphenyl)-5'-methyl-3-styryl-2,3'-bipyridine (formula (IV)) and their mixtures, or one of their pharmaceutically acceptable salts and/or racemic, enantiomeric, diastereoisomeric or tautomeric forms for use in the treatment of a HSP110-associated cancer, especially for use in the treatment of a cancer wherein HSP110 protein is functional for STAT3 phosphorylation and/or wherein HSP110 protein maintains his anti-aggregation activity.

The invention also relates to the use of compound of formula (I), in particular of formula (II), (III) and (IV) as defined above for use in the treatment of colorectal cancer, stomach cancer, endometrial cancer, bladder cancer, urinary tract cancer, ovary cancer, prostate cancer, lymphomas, leukemia, glioblastoma, astrocytoma and neuroblastoma, and preferably colorectal cancer, stomach cancer, endometrial cancer, more preferably colorectal cancer.

The invention also relates to the use of compound of formula (I), in particular of formula (II), (III) and (IV) as defined above for use in the treatment of colorectal cancer, stomach cancer, endometrial cancer, bladder cancer, urinary tract cancer, ovary cancer, prostate cancer, lymphomas, leukemia, glioblastoma, astrocytoma and neuroblastoma, and preferably colorectal cancer, lymphomas, stomach cancer, endometrial cancer, more preferably colorectal cancer and lymphomas.

Lymphomas encompass Diffuse Large B-Cell lymphomas (also termed "DBLCL" herein) and Lymphoplasmacytic lymphoma/Waldenström's macroglobinemia.

A compound according to the invention may be comprised in a composition comprising one or more pharmaceutically acceptable excipients.

Such a composition is considered as a pharmaceutical composition or as a medicament and may more particularly contain an effective dose of at least one compound according to the invention as above defined.

An "effective dose" means an amount sufficient to induce a positive modification in the condition to be treated, but low enough to avoid serious side effects. An effective dose may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound used according to the invention may be administered in an effective dose by any of the accepted modes of administration in the art.

In one embodiment, this compound may be used in a composition intended to be administrated by oral, rectal or parenteral injection route, in particular parenteral injection route such as intravenous or intraperitoneal.

The term "parenteral injection" refers to an administration via injection under or through one or more layers of skin or mucus membranes of an individual. This injection may be for instance intradermal, subcutaneous, intravenous or intramuscular.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, gels, soft and hard gelatine capsules, suppositories, sterile injectable solutions or sterile packages powders.

According to one embodiment, a pharmaceutical composition of the invention may be intended to be administered separately, sequentially or simultaneously with an agent useful for the prevention and/or the treatment of a disease and/or condition related to a HSP110-associated cancer, said agent being distinct from the compound of formula (I) of the invention, in particular different from the compound of formula (II), (III) and (IV).

In a particular embodiment, the compound of formula (I) described above is combined with one or more further anti-cancer agents. As shown in the examples herein, a compound of Formula (I) potentializes the effect(s) of other anti-cancer agents, notably by inducing a synergistic action between the said compound of Formula (I) and the said anti-cancer agent. The examples show that a compound of Formula (I), when used at a dose that does not have an anti-cancer activity (i.e. at a suboptimal dose), is able to substantially enhance the anti-cancer effect of an anti-cancer agent, for instance to substantially enhance the anti-cancer effect of a tyrosine kinase inhibitor, such as Ibrutinib (Ref CAS no 936563-96-1).

In another particular embodiment, a compound according to the invention, as defined above, may be used in combination with one or more other treatment by radiotherapy.

In some embodiments, a compound of formula (I) is combined with one or more anti-cancer agent(s) useful for treating colon or colorectal cancer, and especially human colon or colorectal cancer, such as (i) 5-fluoroacyle-based therapy, leucovorin, oxaliplatin or a combination of the three agents, (ii) capecitabine, oxaliplatin or a combination of both agents or also (iii) irinotecan or ralitrexed.

In some embodiments, a compound of formula (I) is combined with one or more anti-cancer agent(s) useful for treating lymphomas, especially human lymphomas, which includes B-cell lymphomas, such as diffuse large B-cell lymphomas (DLBCL). Such anti-cancer agents encompass rituximab, Ibrutinib, cyclophosphamide, doxorubicin, vincristine, prednisone, and optionally additionally etoposide.

Advantageously, the compound of formula (I) of the present invention is combined with one or more further anticancer agent selected from: 5-fluorouracile-based therapy, abraxane, abarelix, aldesleukin, alemtuzumab, alitretinoin, allopurinol, altretamine, anastrozole, arsenic trioxide, asparaginase, azacitidine, atezolizumab, bevacizumab, bexarotene, bicalutamide, bleomycin, bortezomib, intravenous busulphan, oral busulphan, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, durvalumab, eculizumab, epirubicin, erlotinib, estramustine, etoposide phosphate, etoposide, exemestane, fentanyl citrate, filgrastim, floxuridine, fludarabine, 5-fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alpha 2a, ipilimumab, irinotecan and its derivatives, such as for example nanoliposomal irinotecan (Nal-IRI), lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nivolumab, nofetumomab, oxaliplatin, paclitaxel and its derivatives, such as for example albumin bound paclitaxel (Nab-paclitaxel), pamidronate, panitumumab, pegaspargase, pegfilgrastim, pembrolizumab, pemetrexed disodium, pentostatin, pipobroman, plicamycin, prednisone, procarbazine, quinacrine, rasburicase, ralitrexed, rituximab, sorafenib, streptozocin, sunitinib, sunitinib maleate, tamoxifen, taxol, taxotere, temozolomide, teniposide, testolactone, thalidomide, thioguanine, thiotepa, topotecan, toremifene, tositumomab, trastuzumab, tremelimumab, tretinoin, uracil mustard, valrubicin, vinblastine, vincristine, vinorelbine, vorinostat, Ibrutinib and zoledronate as well as immune checkpoint inhibitors including antibodies against PD1 (programmed cell death-1), PD-L1 (programmed cell death-1-ligand 1), and CTLA4 (cytotoxic T-lymphocyte-associated protein 4).

In particular, the compound of formula (I) of the present invention is combined with at least one other HSP110 inhibitors such as oxaliplatin, 5-fluorouracile-based therapy, or checkpoint inhibitors such as PD-1 inhibitors, PD-L1 inhibitors or CTLA-4 inhibitors.

Methods

Methods for Determining the Responsiveness of a Cancer Patient

As previously specified, the present invention relates to a method for determining the responsiveness of a cancer patient to a HSP110 inhibitor comprising at least the steps of:
a) determining in a sample previously collected from the said patient the ability of said patient to express a functional HSP110 protein.
b) selecting the said patient as responsive to a cancer treatment with a HSP110 inhibitor when said HSP110 protein is functional.

Step a) of the above method may be performed by (a1) extracting the nucleic acids from the tissue sample, in particular tumor tissue, previously collected from the said cancer patient, whereby a nucleic acid sample is provided and then (a2) amplifying and sequencing the nucleic acids encoding HSP110 or a variant thereof contained in the said nucleic acid sample.

Step a) of the above method may also be performed by determining the presence of a HSP110 protein, for example by detecting said protein by several techniques known in the art, such as enzyme-linked immunosorbent assay (ELISA), lateral flow (immuno)assay, western-blotting, mass spectrometry and hydrophobic interaction chromatography (HIC), preferably ELISA or HIC.

Step b) of the above method may be performed by determining if said HSP110 protein is functional for phosphorylating STAT3 protein, and/or if said HSP110 protein maintains his anti-aggregation activity, and/or wherein said HSP110 protein negatively affect the anticancer immune response.

In particular, the present invention relates to a method for determining the responsiveness of a cancer patient to a HSP110 inhibitor comprising at least the steps of:
a) determining, in a nucleic acid-containing sample previously collected from the said patient, the sequence of the HSP110-encoding nucleic acid,
b) selecting the said patient as responsive to a cancer treatment with the HSP110 inhibitor when the sequence determined at step a) encodes a HSP110 protein or variant thereof, which induces tumor cell proliferation and/or the absence of tumor cell death.

More particularly, the present invention relates to a method for determining the responsiveness of a cancer patient to a HSP110 inhibitor comprising at least the steps of:
- a) determining, in a nucleic acid-containing sample previously collected from the said patient, the sequence of the HSP110-encoding nucleic acid, and
- b) selecting the said patient as responsive to a cancer treatment with a HSP110 inhibitor when the sequence determined at step a) encodes HSP110 protein or variant thereof that is functional for phosphorylating STAT3 protein, and/or if said HSP110 protein maintains his anti-aggregation activity, and/or wherein said HSP110 protein negatively affect the anticancer immune response.

Step a) and step b) of the above method are in particular performed as described above.

In another particular embodiment, the present invention relates to a method for determining the responsiveness of a cancer patient to a HSP110 inhibitor comprising at least the steps of:
- a) determining, in a nucleic acid-containing sample previously collected from the said patient, the sequence of the HSP110-encoding nucleic acid, and
- b) selecting the said patient as responsive to a cancer treatment with a HSP110 inhibitor when the sequence determined at step a) encodes a wild-type HSP110 protein.

By wild type HSP110 protein, it is meant the human HSP110 protein described herein, that may for example be referred to the amino acid sequence disclosed in the UniProt sequence database under the reference number Q92598 (SEQ ID NO:1). Regarding a HSP110-encoding nucleic acid, it may be referred to the nucleic acid described in the HGCN database under the name HSPH1 and the reference number 16969.

In a particular embodiment, step b) of the above method may consist of the said patient as responsive to a cancer treatment with a HSP110 inhibitor when the sequence determined at step a) encodes SEQ ID NO:1.

Step a) and step b) of the above method are in particular performed as described above.

Sample previously collected from the said patient may be blood, serum, plasma or tumor tissue, preferably serum or tumor tissue.

Methods for amplifying (e.g. by PCR) and sequencing wild-type HSP110 and variants thereof are well-known in the art.

Amplifying and sequencing wild-type HSP110 and variants thereof may be performed by, e.g., an Amplification Refractory Mutation System (ARMS) or by High Resolution Melt (HRM). ARMS is an amplification strategy in which a polymerase chain reaction (PCR) primer is designed in such a way that it is able to discriminate among templates that differ by a single nucleotide residue. ARMS has also been termed allele-specific PCR or PCR amplification of specific alleles (PASA). Thus, an ARMS primer can be designed to amplify a specific member of a multi-allelic system while remaining refractory to amplification of another allele that may differ by as little as a single base from the former. The main advantage of ARMS is that the amplification step and the diagnostic steps are combined, in that the presence of an amplified product indicates the presence of a particular allele and vice versa. For routine diagnosis, this characteristic of ARMS means that it is a very time-efficient method. High Resolution Melt (HRM) analysis is a powerful technique in molecular biology for the detection of mutations, polymorphisms and epigenetic differences in double-stranded DNA samples. HRM analysis is performed on double stranded DNA samples. Typically, polymerase chain reaction (PCR) will be used prior to HRM analysis to amplify the DNA region in which the mutation of interest lies. Essentially the PCR process turns a tiny amount of the region of DNA of interest into a large amount, so the quantities are large enough for better analysis. In the tube there are now many of copies of the region of DNA of interest. This region that is amplified is known as the amplicon. After the PCR process the HRM analysis begins. The process is simply a precise warming of the amplicon DNA from around 50° C. up to around 95° C. At some point during this process, the melting temperature of the amplicon is reached and the two strands of DNA separate or "melt" apart. The secret of HRM is to monitor this process happening in real-time. This is achieved by using a fluorescent dye. The dyes that are used for HRM are known as intercalating dyes and have a unique property. They bind specifically to double-stranded DNA and when they are bound they fluoresce brightly. In the absence of double stranded DNA, they have nothing to bind to and they only fluoresce at a low level. At the beginning of the HRM analysis there is a high level of fluorescence in the sample because of the billions of copies of the amplicon. But as the sample is heated up and the two strands of DNA melt apart, presence of double stranded DNA decreases and thus fluorescence is reduced. The HRM machine has a camera that watches this process by measuring the fluorescence. The machine then simply plots this data as a graph known as a melt curve, showing the level of fluorescence vs the temperature. The melting temperature of the amplicon at which the two DNA strands come apart is entirely predictable. It is dependent on the sequence of the DNA bases. If you two samples from two different people are compared, they should give exactly the same shaped melt curve. However, if one of the people has a mutation in the amplified DNA region, then this will alter the temperature at which the DNA strands melt apart. So now the two melt curves appear different. The difference may only be tiny, perhaps a fraction of a degree, but because the HRM machine has the ability to monitor this process in "high resolution", it is possible to accurately document these changes and therefore identify if a mutation is present or not.

The above methods allow predicting response to a treatment by an HSP110 inhibitor.

In some embodiments, it may be used a forward primer, a reverse primer, and optionally a probe, for amplifying and sequencing wild-type HSP110 or a variant thereof. In particular, the forward primer may have the sequence 5'-GC-TACACGAATTCCAGCTGTGA-3' (SEQ ID NO: 7), the reverse primer may have the sequence 5'-GAGCAG-CATGGTTTCGACTAAA-3' (SEQ ID NO: 8). Preferably, the appropriate probe(s), when present, are labelled with at least one fluorescent label or dye well known in the art. For performing step a) of the method, the skilled artisan mat notably refer to the Canadian patent application number CA 2 830 787 in the names of Université de Bourgogne and INSERM.

At step a), sequencing the amplified nucleic acid encoding HPSP110 or variant thereof may be performed by any method known in the art, such as by the Sanger's method, the Maxam and Gilbert method or by using an automatic DNA sequencer or by using capillary gel electrophoresis. It may for example be referred to the review of Heather et al. (2016, Genomics, Vol. 107 (n° 1): 1-8).

Methods for selecting the said patient as responsive to a cancer treatment with a HSP110 inhibitor when the sequence determined at step a) encodes an HSP110 protein or variant thereof that is functional for phosphorylating STAT3 are well known in the art. An illustrative method for determining the ability of a HSP110 protein or variant thereof to phosphorylate human STAT3 is disclosed in the examples herein and is more generally described herein.

A HSP110 inhibitor is a compound of formula (I) as described above, and which interact with HSP110 protein.

In particular, the present invention relates to a method wherein the said HSP110 inhibitor is a compound of general formula (I):

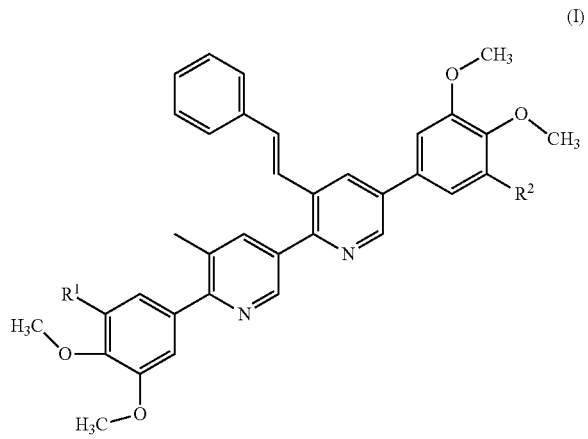

wherein $R^1$ and $R^2$ represent independently a group selected among H and a (C1-C3) alkoxy group; or one of its pharmaceutically acceptable salts and/or racemic, enantiomeric, diastereoisomeric or tautomeric forms. Various embodiments of a compound of formula (I) are described elsewhere in the present disclosure.

In a particular embodiment, the compound of formula (I) is preferably selected from of (E)-6'-(3,4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine(formula (III)), (E)-5,6'-Bis(3,4-dimethoxyphenyl)-5'-methyl-3-styryl-2,3'-bipyridine (formula (IV)) and their mixtures, or one of their pharmaceutically acceptable salts and/or racemic, enantiomeric, diastereoisomeric or tautomeric forms.

A mutation in the HSP110-encoding nucleic acid causing an amino acid change in the nucleotide-binding domain according to the present invention is a mutation which prevents the phosphorylation of STAT 3 protein.

Examples of sequence of the HSP110-encoding nucleic acid which encodes a HSP110 protein or variant thereof that is not functional for phosphorylating STAT3 protein correspond to the sequences with deletions affecting a microsatellite repeat of 17 thymidine nucleotides localized in the splicing acceptor site of intron 8 of the HSPH1 gene, i.e the gene coding the HSP110 protein.

This mutation leads to the skipping of exon 9 and thus to the production of a truncated form of HSP110 protein lacking amino acids 381 to 858 of the wild-type HSP110 protein. In a preferred embodiment, the mutated HSP110 protein lacks the domain consisting of amino acids 381 to 858 of SEQ ID NO:1. For example, the truncated form of HSP110 corresponds to SEQ ID NO: 9. In another preferred embodiment, the mutated HSP110 protein is encoded by an mRNA lacking exon 9. Exon 9 of the gene coding for HSP110 is for example described between positions 1536 and 1642 in the NCBI Reference sequence NM_006644.2 (published version at Dec. 27, 2010). This particular alternative splicing process takes place at the detriment of wild type HSP110 and therefore the truncated form has been identified as a pro-apoptotic protein. This truncated form is present in colorectal cancers of the type MSI (microsatellite instable) and is thus inactive. Patients with microsatellite instable type with an excellent prognosis associated to the mutation/inactivation of HSP110 (Collura et al, Gastroenterol 2014) are not responsive to a cancer treatment with a HSP110 inhibitor according to the invention. This mutation is further described in WO2012/127062 and in "Expression of a mutant HSP110 sensitizes colorectal cancer cells to chemotherapy and improves disease prognosis" (Dorard et al 2011, Nature Medicine, doi:10.1038/nm.2457). In a particular embodiment, patients with a MSI type which have a low level of expression of the mutant, can benefit of the treatment with the compounds of the present invention.

Patients with a MSI type may be for example determined by looking at microsatellite instability in a panel of five genetic microsatellite markers in a tumor: BAT25, BAT26, NR21, NR24 and NR27. Patients with instability at two or more of these markers are defined as being MSI-High (MSI-H), whereas those with instability at one marker or showing no instability were respectively defined as MSI-Low (MSI-L) and Microsatellite Stable (MSS) tumors (Duval and Hamelin, Annates de genetique 45: 71-75 (2002)). Detecting whether microsatellite instability is present may for example be performed by genotyping microsatellite markers, such as BAT25, BAT26, NR21, NR24 and NR27, e.g. as described in Buhard et al., J Clin Oncol 24 (2), 241 (2006) and in European patent application No. EP 1 1 305 160.1. A cancer is defined as having a MSI phenotype if instability is detected in at least 2 microsatellite markers. To the contrary, if instability is detected in one or no microsatellite marker, then said cancer has a MSS phenotype.

According to the invention, patients with a microsatellite stable type (MSS) or a microsatellite instable low (MSI-Low) type are selected as responsive to a cancer treatment with a HSP110 inhibitor.

In a particular embodiment, the present invention relates to a method for determining the responsiveness of a cancer patient to a HSP110 inhibitor comprising at least the steps of:
  a) determining, in a nucleic acid-containing sample previously collected from the said patient, the sequence of the HSP110-encoding nucleic acid, and
  b) selecting the said patient as responsive to a cancer treatment with a HSP110 inhibitor when the amount of wild-type HSP110 protein is higher than the amount of truncated HSP110 protein in the said sample.

Step a) and step b) of the above method are in particular performed as described above.

In particular, the present invention relates to a method for determining the responsiveness of a cancer patient to a HSP110 inhibitor comprising at least the steps of:
  a) determining, in a nucleic acid-containing sample previously collected from the said patient, the sequence of the HSP110-encoding nucleic acid, and
  b) selecting the said patient as responsive to a cancer treatment with a HSP110 inhibitor when the patient has a microsatellite stable type or a microsatellite instable low type.

Step a) of the above method may be performed as described above.

Step b) of the above method may be performed as described above, for example by determining if said HSP110 is functional of phosphorylating STAT3 protein, in particular in a tumor tissue sample.

Methods for Treating an Individual

This invention also concerns a method for treating an individual affected with a HSP110-associated cancer comprising a step of administering to the said individual a HSP110 inhibitor as described herein, and especially a HSP110 inhibitor of Formula (I).

This invention further relates to a HSP110 inhibitor, and especially a HSP110 inhibitor of Formula (I), for use in the treatment of a HSP110-associated cancer.

This invention also concerns the use of a HSP110 inhibitor, and especially a HSP110 inhibitor of Formula (I), for preparing a medicament for treating a HSP110-associated cancer.

The present invention also relates to a method for treating an individual affected with a HSP110-associated cancer comprising the steps of:
  a) determining the responsiveness of a cancer patient to a HSP110 inhibitor comprising at least the steps of:
    a1) determining, in a sample previously collected from the said patient, the ability of said patient to express a functional HSP110 protein;
    a2) selecting the said patient as responsive to a cancer treatment with a HSP110 inhibitor when said HSP110 protein is functional, and
  b) administering an anti-cancer treatment to the said patient when selected as responsive to a cancer treatment with a HSP110 inhibitor at step a2).

The present invention also relates to a method for treating an individual affected with a HSP110-associated cancer comprising the steps of:
  a) determining the responsiveness of a cancer patient to a HSP110 inhibitor comprising at least the steps of:
    a1) determining, in a nucleic acid-containing sample previously collected from the said patient, the sequence of the HSP110-encoding nucleic acid;
    a2) selecting the said patient as responsive to a cancer treatment with a HSP110 inhibitor when the sequence determined at step a) encodes an HSP110 protein or variant thereof that is functional for phosphorylating STAT3, and
  b) administering an anti-cancer treatment to the said patient when selected as responsive to a cancer treatment with a HSP110 inhibitor at step a2).

This invention also concerns a method for determining responsiveness of a cancer patient to a HSP110 inhibitor comprising the steps of:
  a) preparing a cell lysate from the tumor tissue previously collected from the said cancer patient;
  b) detecting phosphorylated STAT3 protein in the said cell lysate, e.g. by using antibodies binding specifically to phosphorylated STAT3 protein, and
  c) selecting the said patient as responsive to a cancer treatment with a HSP110 inhibitor when phosphorylated STAT3 is detected at step b).

This invention also relates to a method for treating an individual affected with a HSP110-associated cancer comprising the steps of:
  a) determining the responsiveness of a cancer patient to a HSP110 inhibitor comprising at least the steps of:
    a1) preparing a cell lysate from the tumor tissue previously collected from the said cancer patient;
    a2) detecting phosphorylated STAT3 protein in the said cell lysate, e.g. by using antibodies binding specifically to phosphorylated STAT3 protein;
    a3) selecting the said patient as responsive to a cancer treatment with a HSP110 inhibitor when phosphorylated STAT3 is detected at step a2), and
  b) administering an anti-cancer treatment to the said patient when selected as responsive to a cancer treatment with a HSP110 inhibitor at step a3).

Embodiments of the above method are described elsewhere in the present specification.

HSP110 inhibitor of the present invention is a compound able to bind to the HSP110 protein and prevent STAT3 protein phosphorylation.

In particular, the HSP110 inhibitor of the present invention is a compound of formula (I):

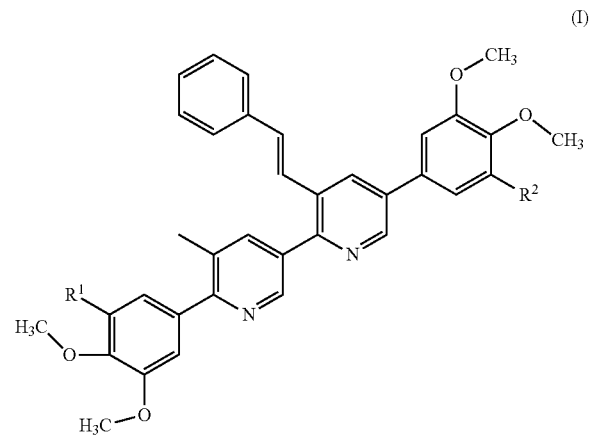

wherein:
  $R^1$ and $R^2$ represent independently a group selected among H and a (C1-C3) alkoxy group;

or one of its pharmaceutically acceptable salts and/or racemic, enantiomeric, diastereoisomeric or tautomeric forms. Various embodiments of a compound of formula (I) are described elsewhere in the present disclosure.

In a particular embodiment, the compound of formula (I) is preferably selected from (E)-6'-(3,4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine(formula (III)), (E)-5,6'-Bis(3,4-dimethoxyphenyl)-5'-methyl-3-styryl-2,3'-bipyridine (formula (IV)) and their mixtures, or one of their pharmaceutically acceptable salts and/or racemic, enantiomeric, diastereoisomeric or tautomeric forms.

Sequence described in the present invention corresponds to the following sequence:

```
Full sequence of HSP110 protein
                            SEQ ID NO: 1
MSVVGLDVGSQSCYIAVARAGGIETIANEFSDRCT

PSVISFGSKNRTIGVAAKNQQITHANNTVSNFKRF

HGRAFNDPFIQKEKENLSYDLVPLKNGGVGIKVMY

MGEEHLFSVEQITAMLLTKLKETAENSLKKPVTDC

VISVPSFFTDAERRSVLDAAQIVGLNCLRLMNDMT
```

-continued

```
AVALNYGIYKQDLPSLDEKPRIVVFVDMGHSAFQV

SACAFNKGKLKVLGTAFDPFLGGKNFDEKLVEHFC

AEFKTKYKLDAKSKIRALLRLYQECEKLKKLMSSN

STDLPLNIECFMNDKDVSGKMNRSQFEELCAELLQ

KIEVPLYSLLEQTHLKVEDVSAVEIVGGATRIPAV

KERIAKFFGKDISTTLNADEAVARGCALQCAILSP

AFKVREFSVTDAVPFPISLIWNHDSEDTEGVHEVF

SRNHAAPFSKVLTFLRRGPFELEAFYSDPQGVPYP

EAKIGRFVVQNVSAQKDGEKSRVKVKVRVNTHGIF

TISTASMVEKVPTEENEMSSEADMECLNQRPPENP

DTDKNVQQDNSEAGTQPQVQTDAQQTSQSPPSPEL

TSEENKIPDADKANEKKVDQPPEAKKPKIKVVNVE

LPIEANLVWQLGKDLLNMYIETEGKMIMQDKLEKE

RNDAKNAVEEYVYEFRDKLCGPYEKFICEQDHQNF

LRLLTETEDWLYEEGEDQAKQAYVDKLEELMKIGT

PVKVRFQEAEERPKMFEELGQRLQHYAKIAADFRN

KDEKYNHIDESEMKKVEKSVNEVMEWMNNVMNAQA

KKSLDQDPVVRAQEIKTKIKELNNTCEPVVTQPKP

KIESPKLERTPNGPNIDKKEEDLEDKNNFGAEPPH

QNGECYPNEKNSVNMDLD

Amino acids 1 to 378 of SEQ ID NO 1
(ATP binding domain)
                                SEQ ID NO: 2
MSVVGLDVGSQSCYIAVARAGGIETIANEFSDRCT

PSVISFGSKNRTIGVAAKNQQITHANNTVSNFKRF

HGRAFNDPFIQKEKENLSYDLVPLKNGGVGIKVMY

MGEEHLFSVEQITAMLLTKLKETAENSLKKPVTDC

VISVPSFFTDAERRSVLDAAQIVGLNCLRLMNDMT

AVALNYGIYKQDLPSLDEKPRIVVFVDMGHSAFQV

SACAFNKGKLKVLGTAFDPFLGGKNFDEKLVEHFC

AEFKTKYKLDAKSKIRALLRLYQECEKLKKLMSSN

STDLPLNIECFMNDKDVSGKMNRSQFEELCAELLQ

KIEVPLYSLLEQTHLKVEDVSAVEIVGGATRIPAV

KERIAKFFGKDISTTLNADEAVARGCAL

Amino acids 184 to 193 of SEQ ID NO 1
                                SEQ ID NO: 3
YKQDLPSLDE Amino acids 275 to 284 of SEQ ID NO 1
                                SEQ ID NO: 4
KLMSSNSTDL Amino acids 341 to 355 of SEQ ID NO 1
                                SEQ ID NO: 5
VGGATRIPAVKERIA Amino acids 360 to 364 of SEQ ID NO 1
                                SEQ ID NO: 6
KDIST Primer for WT HSP110
                                SEQ ID NO: 7
GCTACACGAATTCCAGCTGTGA Reverse primer for HSP110
                                SEQ ID NO: 8
GAGCAGCATGGTTTCGACTAAA Truncated HSP110 protein
                                SEQ ID NO: 9
MSVVGLDVGSQSCYIAVARAGGIETIANEFSDRCT

PSVISFGSKNRTIGVAAKNQQITHANNTVSNFKRF

HGRAFNDPFIQKEKENLSYDLVPLKNGGVGIKVMY

MGEEHLFSVEQITAMLLTKLKETAENSLKKPVTDC

VISVPSFFTDAERRSVLDAAQIVGLNCLRLMNDMT

AVALNYGIYKQDLPSLDEKPRIVVFVDMGHSAFQV

SACAFNKGKLKVLGTAFDPFLGGKNFDEKLVEHFC

AEFKTKYKLDAKSKIRALLRLYQECEKLKKLMSSN

STDLPLNIECFMNDKDVSGKMNRSQFEELCAELLQ

KIEVPLYSLLEQTHLKVEDVSAVEIVGGATRIPAV

KERIAKFFGKDISTTLNADEAVARGCALQC
```

The present invention will be better understood by referring to the following examples and figures which are provided for illustrative purpose only and should not be interpreted as limiting in any manner the instant invention.

EXAMPLES

Example 1: In Vitro Efficacity of Compounds of Formula (I)

The efficiency of the compounds of formula (II) (named compound 33), of formula (III) (named compound 52) and of formula (IV) (named compound 51) of the invention to:
- block HSP110 proteins anti-aggregation role has been evaluated by using a well-known test of substrate competition,
- interact with HSP110 and inhibit STAT3 phosphorylation, has been evaluated by using a well-known test of immunoprecipitation.

Tests were realized using a comparative compound (named compound 61) and compounds of the invention, in particular compounds of formula (II), (III), (IV). (Table 2)

TABLE 2
Compound of formula (II), named compound 33
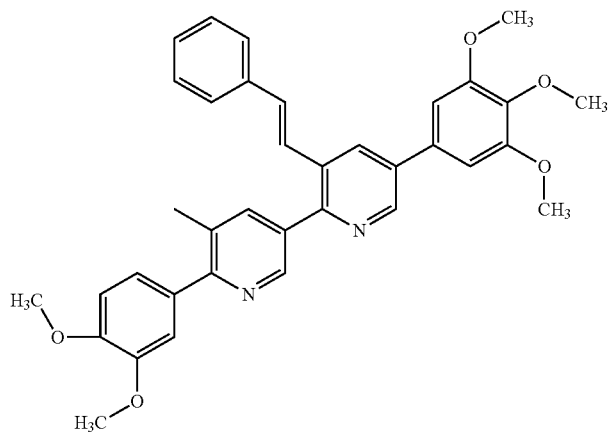
Compound of formula (III), named compound 52
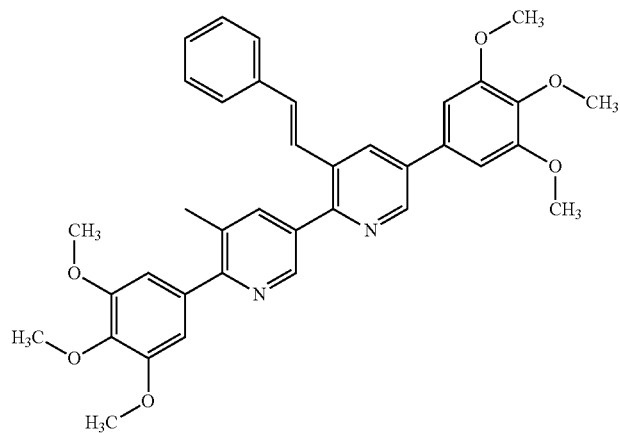
Compound of formula (IV), named compound 51.
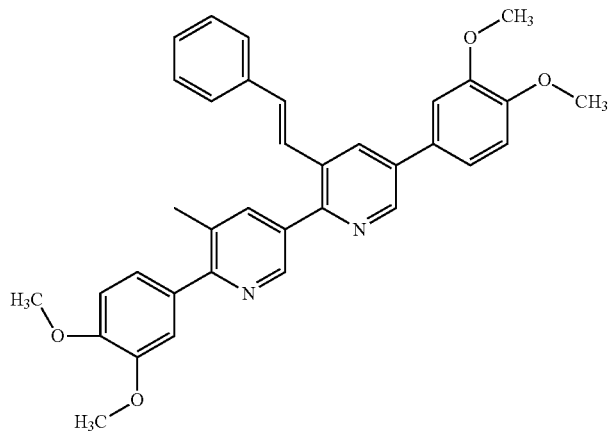
Comparative Compound, named compound 61
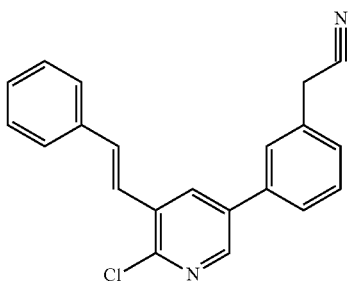 [SMILES: N#CCc1cccc(-c2cnc(Cl)c(/C=C/c3ccccc3)c2)c1]

Compounds were prepared by adaptation of known methods and especially by methods described in document number WO2015132727. Compound 61 is relative to (E)-2-(3-(6-Chloro-5-styrylpyridin-3-yl) phenyl) acetonitrile.

Compounds were dissolved in DMSO and stored at −20° C. To achieve the concentrations of 10 μM, compounds were diluted in culture medium (for cells assays) or reaction buffer (for in vitro assays). Controls with and without DMSO (maximal 0.1% for cells and 0.5% for in vitro) were carried out in each assay.

The production of NBD-HSP110 (Nucleotide Binding Domain HSP110) was performed by using DNA coding the NBD-HSP110 (from human-HSP110; uniprot ID Q92598) codon-optimized for *Escherichia coli* (*E. coli*) heterologous expression. The NBD-HSP110 was subcloned in pET21a using NdeI and SacI as restriction site respectively in 5' and 3'. The *E. coli* BL21 star (DE3) (from Novagen) was transformed with pET21a-NBDHSP110.

Anti-aggregation function of HSP110 was evaluated as described by O H et al (*The Journal of biological chemistry* 274, 15712-15718 (1999)). The human protein HSP110 (obtained as described above) at a concentration of 1.5 μM was incubated with firefly luciferase (from Sigma—from *Photinus pyralis*) in reaction buffer and heated in water bath for 30 min at 42° C.

Compounds of the present invention were added in reaction buffer to achieve the indicated concentrations and the final DMSO concentration was held constant at 1%. The heated reaction was diluted 10 times into buffer containing 60% of rabbit reticulocytelysate and incubated for 2 hours. The luciferase activity was measured by diluting 5 times the solution in HEPES and adding 5 μL of the solution in luciferase substrate (50 μL of Luciferase Assay System—Promega E1501 diluted in HEPES). The bioluminescence was reading with Envision Perkin Elmer.

The percentage of activity (x) was calculated by using the following equation: $x=[(A-B)/(C-B)]\times 100$, where (A) is the luciferase luminescence in presence of compounds of the invention, (B) in absence of HSP110 and (C) in presence of DMSO (Control). The percentage of total folding HSP110-promoted (mean=36%) was calculated considering as 100% the luminescence of luciferase incubated with HSP110 without heat shock. The IC50 were calculated from the dose-response curves, which were fitted by GraphPrism (Equation: $Y=100/(1+10^{((\text{Log IC50}-X)*\text{HillSlope})})$).

Figure 1:
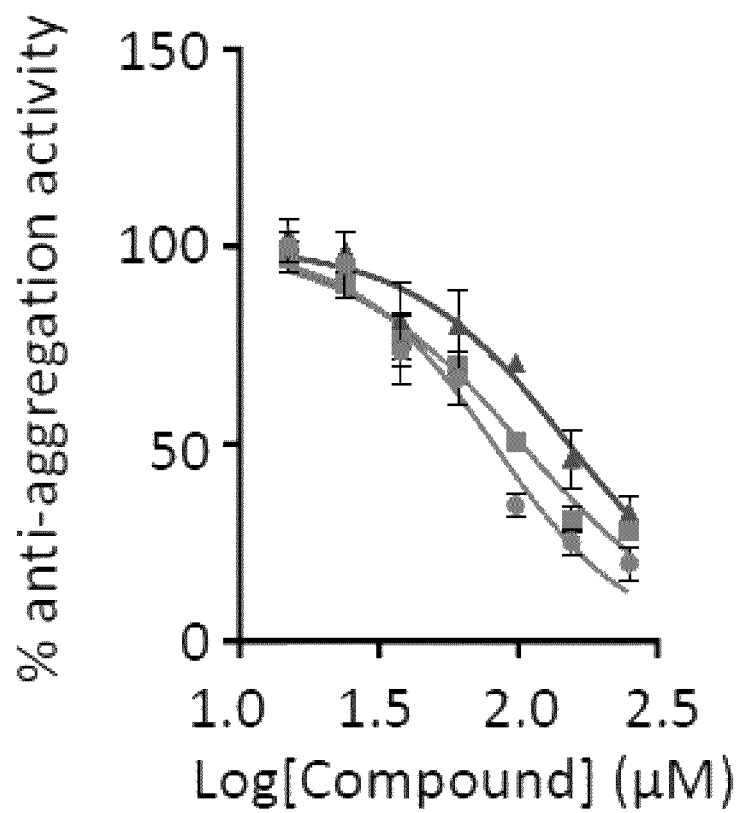
FIG. 1:
Percentage of the anti-aggregating activity in function of Log of concentration of compound in μM (Abscissa: Log [Compound] in μM (scale 0.5); Ordinate: Percentage of anti-aggregation activity (scale 50)). Spot symbol (●) line compound 33 relative to formula (II), square symbol (■) line compound 52 relative to formula (III), triangle symbol (▲) line compound 61 relative comparative compound. IC50 of compound 33 is 58.3±1.7 μM (with $R^2=0.97$), IC50 of compound 52 is IC50=86.0±1.5 μM (with $R^2=0.98$), IC50 of compound 61 is IC50=227.5±1.9 μM (with an $R^2=0.97$).

As presented in FIG. 1, compounds were able to significantly inhibit HSP110 anti-aggregating activity with IC50 values estimated at 58.3±1.7 μM, for compounds 33 (formula (II)), 86.0±1.5 μM for compound 52 (formula (III), and 227.5±1.9 μM for compound 61. Moreover, these compounds seemed specific for HSP110 since no inhibition was observed when we checked the refolding activity of other HSPs such as HSP70. Compound 61 has a lower anti-aggregation inhibition effect than compound of the present invention.

These results show that compounds 33 and 52 affect the general chaperone anti-aggregation function of HSP110 (FIG. 1). As explained HSP110 is part of a chaperone network that, is essential for the cancer cells' survival.

Colorectal cells lines were purchased from the American Type Culture Collection. CT-26 and HCT116 were cultured in Roswell Park Memorial Institute 1640 medium. SW480 cells were engineering to express a control (SHC016-1EA) or a hsph1 targeting shRNA (TRCN0000275617) using Sigma Aldrich Mission pLKO.1 hPGK-Puro-CMV-tGFP plasmids and were in cultured in high-glucose Dulbecco's modified Eagle medium containing puromycin (2.5 μg/mL) as selecting agent and 10% SBF, 100 U/mL penicillin, 100 μg/mL streptomycin and 0.25 μg/mL amphotericin B.

Proliferation was determined by staining cells with Cell Trace Violet (Invitrogen-C34557) according to the manufacturer's procedure. Cell divisions were detected over 96 h by flow cytometry (LSRII cytometer) and the number of cell generations was estimated by ModFit software. Death cells were excluded from analysis by labeling with AnnexinV-FITC (BD Pharmigen-556419) and 206 7-AAD (eBioscience-00-6993-50) according to the manufacturer's procedure.

Immunoprecipitation test were realized on human colorectal cancer cells (SW480 and HCT116 cell lines), using a control depleted in HSP110 called Sh110 and a not depleted cells in HSP110. STAT3 phosphorylation is then induced by compounds 33 and 52. Depletion of HSP110 in the negative control blocked the phosphorylation of STAT3 without affecting STAT3 overall levels (FIGS. 2 and 3).

Figure 2A:
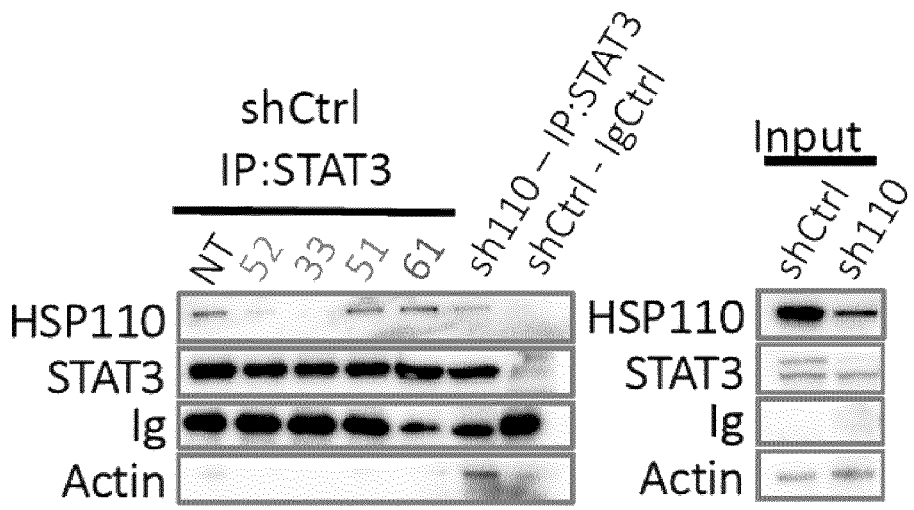
FIG. 2A: Immunoprecipitation (IP) analysis of HSP110 protein (first line), STAT3 protein (second line) compared with total Immunoglobuline (Ig) and actin in SW480 cells treated with (from left to the right column) non-relevant antibody as control (called NT a Normal rabbit IgG (sc-2027) from Santa Cruz Biotechnologies), compound 52 (related to formula (III)), compound 33 (related to formula (II)), compound 51 (related to formula (IV)) and comparative compound 61 at a concentration of 10 μM during 48 h on shCtrl cells transfected with shRNA for shRNA control (referenced ShCtrl IP:STAT3 for the five first columns) or HSP110-silencing (sh110) (referenced sh110-IP:STAT3 for the two last columns) (from the left to the right columns). Immunoprecipitation analysis of HSP110 (first line), STAT3 (second line) compared with total Ig and actin (second blot in the right) is observed with shCtrl cells transfected with shRNA for shRNA control (shCtrl) or HSP110-silencing (sh110) (left to right columns).
Figure 2B:
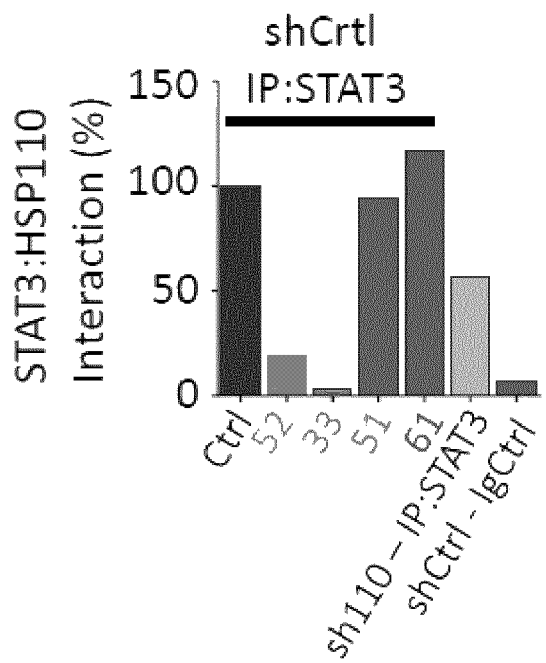
FIG. 2B: Quantification of HSP110:STAT3 disruption in percentage considering the total amount of HSP110 protein normalized by the signal intensity of the Ig band of FIG. 1 panel A. (Ordinate: Percentage of STAT3:HSP110 protein interaction (scale 50)). The histogram measured quantification in percentage for ShCtrl IP: STAT3 treated with Ctrl, compounds 52, 33, 51 and comparative compound 61, and for shCtrl cells transfected with shRNA for shRNA control referenced ShCtrl IP: STAT3) or HSP110-silencing (sh110) (referenced sh110-IP: STAT3) (from the left to the right column)
Figure 3A:
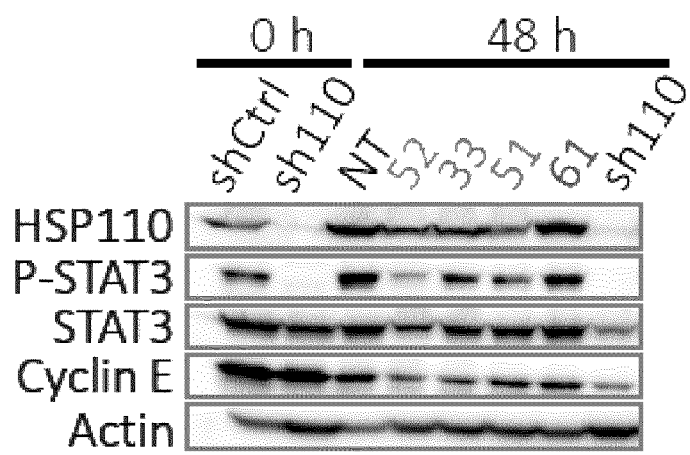
FIG. 3A: Immunoprecipitation analysis of HSP110 (first line), Phosphorylated-STAT3 protein (P-STAT3) (second line), STAT3 (third line), Cyclin E (fourth line) and Actin (last line) on SW480 cells: Immunoblot shows precipitation at 0 h shCtrl cells transfected with shRNA for shRNA control (shCtrl) or HSP110-silencing (sh110) (respectively first and second columns). Results for SW480 cells treated during 48 h with non-relevant antibody (called NT), compound 52, compound 33, compound 51 and comparative compound 61 at 10 µM, and sh110 cells correspond to the third fourth, fifth, sixth and last columns from the left to the right.
Figure 3B:
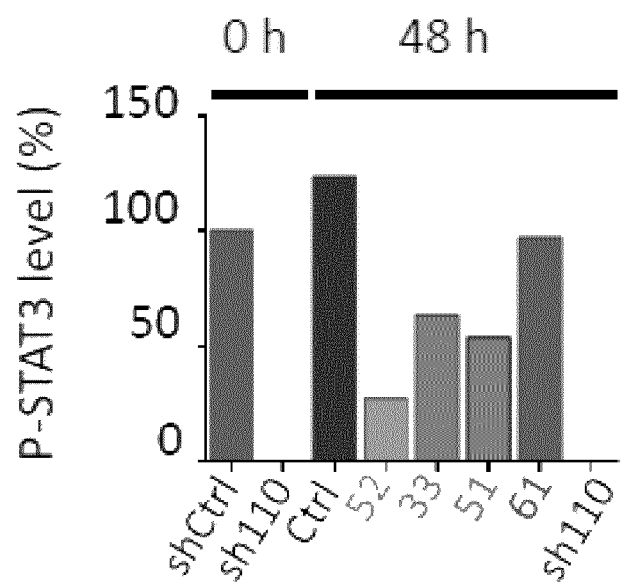
FIG. 3B: Quantification of P-STAT3 level (in percentage) normalized by actin. The histogram shows quantification in percentage at 0 h shCtrl cells transfected with shRNA for shRNA control (shCtrl) or HSP110-silencing (sh110) (respectively the first and second colum). The histogram shows quantification for SW480 cells treated during 48 h with non-relevant antibody which is DMSO (called NT), compound 52, compound 33, and compound 51 and comparative compound 61 at a concentration of 10 µM and sh110 cells (from the third to the last columns on the left to the right). (Ordinate: Percentage of P-STAT3 level (scale 50)

Results confirm compounds 33 and 52 were capable of disrupting HSP110:STAT3 complex within the cell using human colorectal SW480 cancer cells (FIG. 2 A-B). Indeed, percentage of interaction of STAT3:HSP110 is low for compounds 33 and 52 (respectively 20 and 5%) compared to compounds 51 and 61 that seems to not decrease the interaction STAT3:HSP110, according to the percentage of interaction measured in FIG. 1. Similarly, compounds 33 and 52, but not compound 61, decreased the amount of PSTAT3 (phosphorylated STAT3) with about 20% of P-STAT3 level for compound 52 and 60% for compound 33 (FIG. 3 A-B). Surprisingly, we see that the compound 51 decreases the level of phosphorylated STAT3, at about 50% compared to compound 61 at 100% (as the ShCtrl) (FIG. 3, Panel B, bottom figure and Panel A).

Figure 4A:
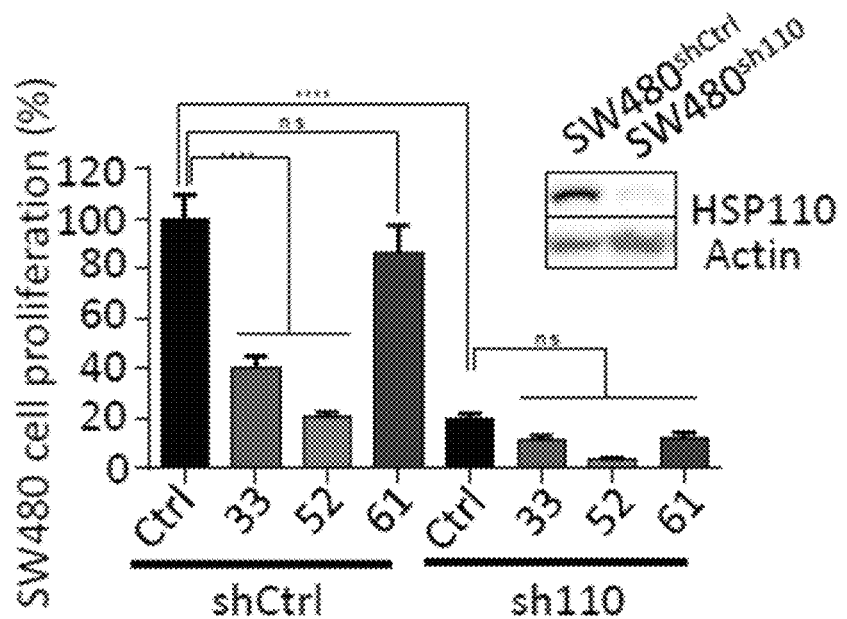
FIG. 4A: Relative quantification of cell proliferation in SW480 cells transfected with shRNA for shRNA control (shCtrl) (from the first to the fourth columns from left to right) or HSP110-silencing (sh110) (from the fifth to the last columns, from left to right) treated with Ctrl (DMSO), compound 33, compound 52, and comparative compound 61 at a concentration of 10 µM during 96 h (Histogram columns from the left to the right). Ordinate: Percentage of SW480 cell proliferation (scale 20) for the upper figure; Statistical analysis has been performed by ANOVA : ($p<0.05$); *: $p<0.005$. Western blot of HSP110 and actin (first and second line of blots) for the shCtrl SW480 cells and sh110 SW480 cells (first and second columns).
Figure 4B:
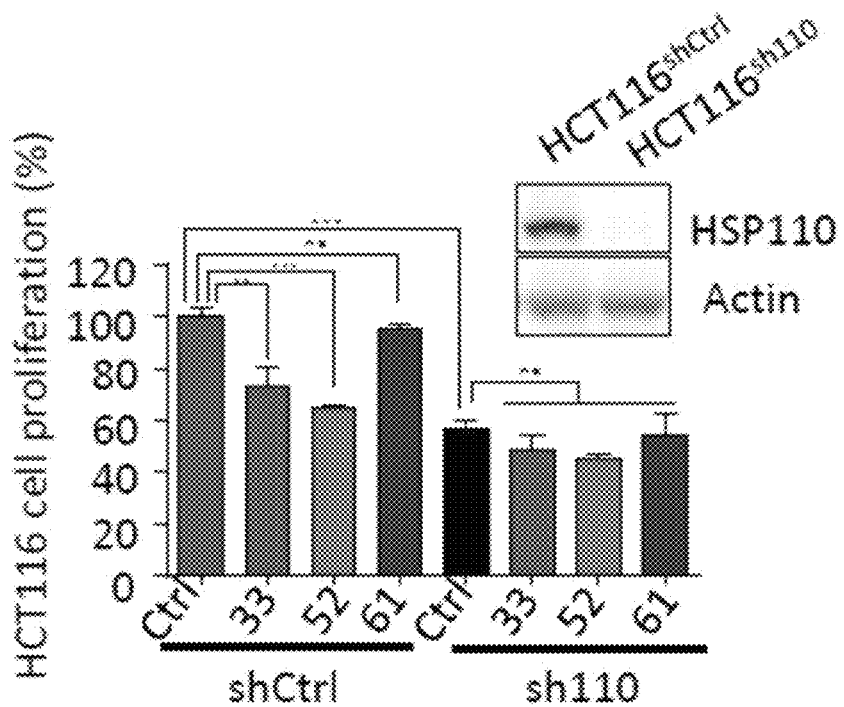
FIG. 4B: Relative quantification of cell proliferation in HCT116 cells transfected with shRNA for shRNA control (shCtrl) (from the first to the fourth columns from left to right) or HSP110-silencing (sh110) ((from the fifth to the last columns, from left to right) left to right) treated with Ctrl (DMSO), compound 33, compound 52, and comparative compound 61 at a concentration of 10 µM during 96 h (Histogram from the left to the right). Ordinate: Percentage of HCT116 cell proliferation (scale 20) for the lower figure. Statistical analysis has been performed by ANOVA : ($p<0.05$); *: $p<0.005$. Western blot of HSP110 and actin (first and second line of blots) for the shCtrl HCT116 cells and sh110 HCT116 cells (first and second columns).

We determined the effect of the compounds 33, 52 and 61 in the proliferation of human colorectal SW480 and HCT116 cancer cells after 96 h of treatment (FIG. 4 A-B). The decreased of cell proliferation was analyzed by using the depletion of HSP110 by means of a specific shRNA (FIG. 4 A-B). In cells transfected with a shRNA control (and therefore expressing HSP110), compounds 33 and 52 were able to hamper cell proliferation by 60% and 82% for the SW480 cells and by around 40% for the HCT116. Rates of inhibition in cell proliferation obtained by treatment with these compounds were similar to that obtained by depletion of HSP110 (shRNA-mediated) (FIG. 4 A-B). Altogether, these results strongly suggested that the effect of the compounds of the present invention inhibit colorectal cancer cells growth, by blocking HSP110 function, especially HSP110 interaction with STAT3 and anti-aggregation function.

Figure 5A:
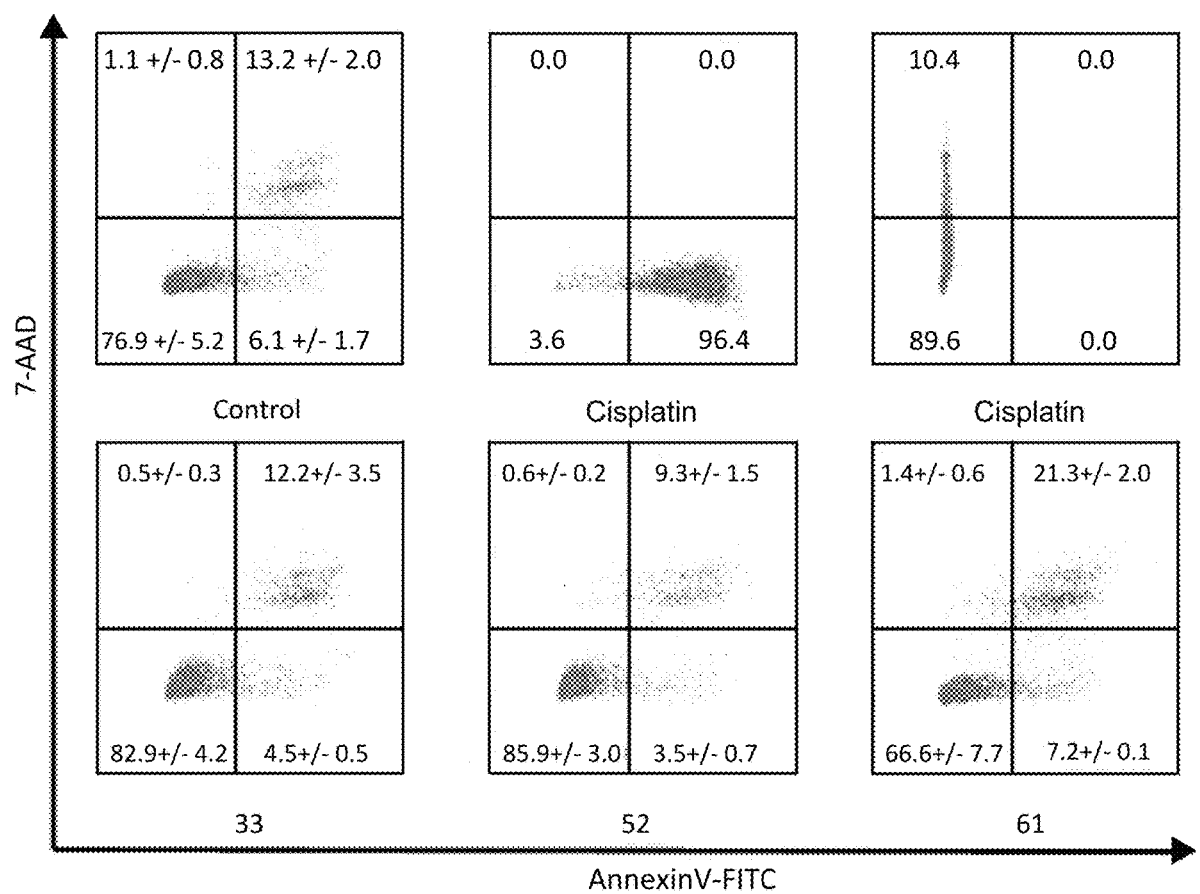
FIG. 5A: Flow cytometric analysis of cell death in CT26 cells treated with the compound 33 (at the bottom left), compound 52 (at the bottom middle), comparative compound 61 (at the bottom right) at 10 µM during 96 h compared with Control (DMSO) (at the top left), and Cisplatin (at the top middle and top right). Live cells were double negative for 7-AAD (Y axis) and Annexin V (X axis), early apoptotic cells were positive for Annexin V, late apoptotic cells were positive for Annexin V and 7-AAD (top left quadrant) and dead cells were positive for 7-AAD only.
Figure 5B:
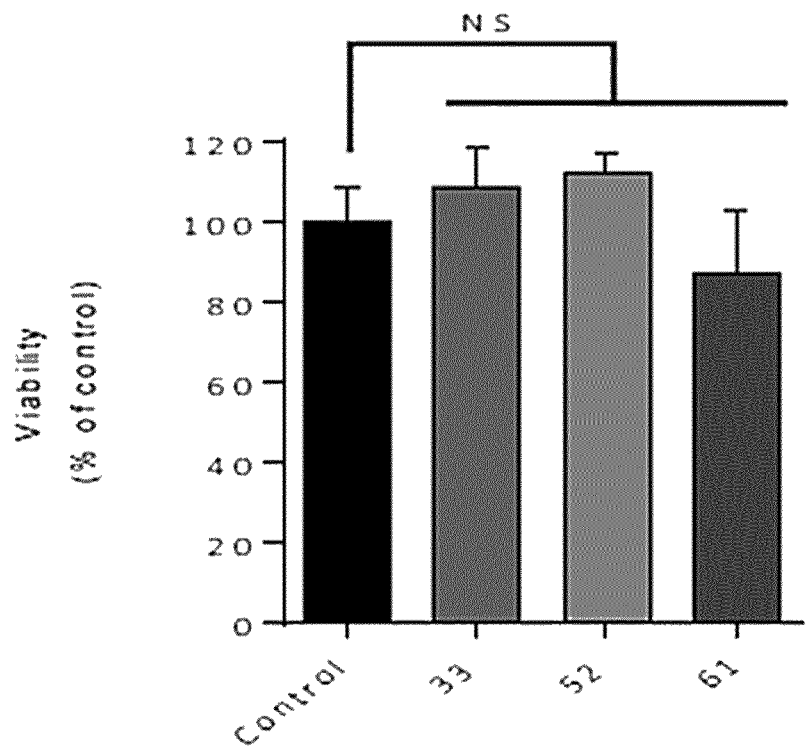
FIG. 5B: Quantification of cell viability (in percentage) from flow cytometry data are represented (Control, cells, compounds 33, 52 and 61 from the left to the right bars). (Abscissa Negativity of 7-AAD; Ordinate Negativity of Annexin V).

We then analyzed cell death in CT26 cells treated with 10 μM during 96 h of compounds 33, 52 and 61 by flow cytometry. Cells were also treated with a well know anti-cancer compound, called cisplatin. Cells were marked for 7-aminoactinomycin D, which exclusively bind on death cells and for Annexin V, a well-known indicators of early stage apoptosis, thanks to its ability to bind to phosphatidylserine. As seen, for compound 33, 52 and 61, compared to cisplatin compound, cancer cells don't seem to be marked with marker Annexin and 7-AAD. Moreover, the quantification (FIG. 5 A-B) shows the non-significativeness of this test in vitro.

It is worth noting treatment with compound 33 and 52 in vitro does not allow detecting signifcally apoptosis, (FIG. 5 A-B) in comparison with control and Cisplatin.

Example 2: In Vivo Efficacity of Compound of Formula (II), Also Named Compound 33

In this example, the in vivo efficacy of compound (II) of the invention is testing using a tumor growth analysis and tumor immunohistochemistry.

Figure 6A:
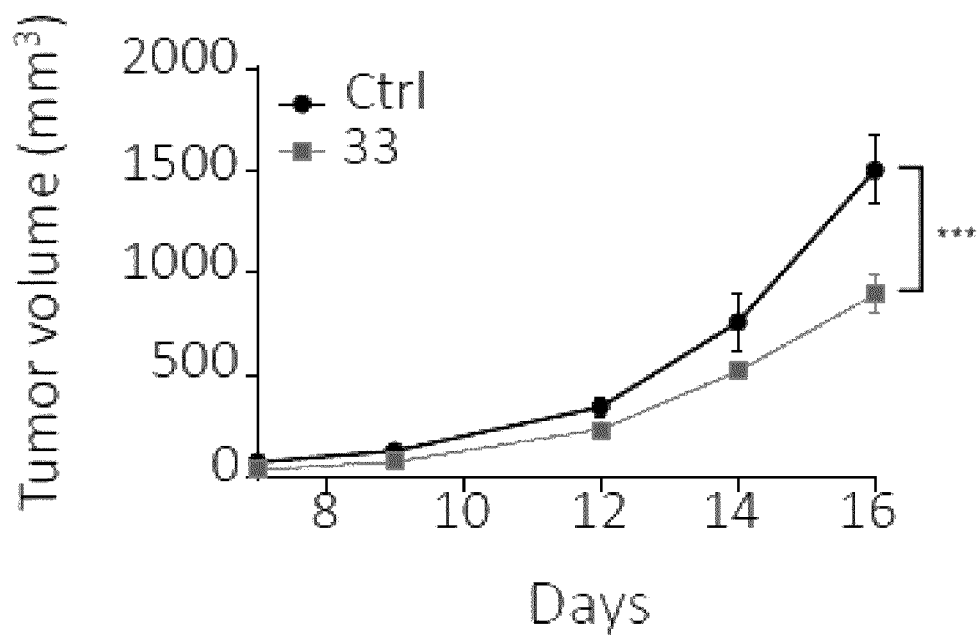
FIG. 6A: Tumor volume monitoring of CT26 cells in Balb/c mice control-treated (Ctrl—line with circle) and treated with the compound 33 (5 mg/kg—line with square). Animals were treated by intraperitoneally injection every three days. (Abscissa: Days from 0 to 16 in day; Ordinate: Tumor volume in $mm^3$ from 0 to 200 (scale 500))
Figure 6B:
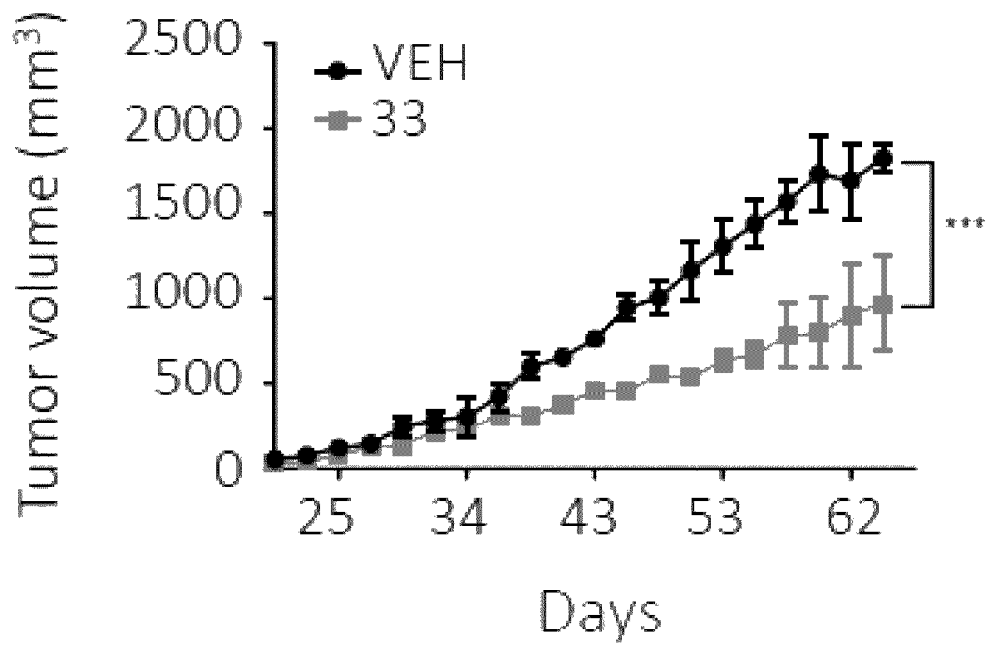
FIG. 6B: Tumor volume monitoring of HCT116 cells grown in NOD/SCID animals treated intraperitoneally either with a non-relevant compound which is DMSO (named VEH line with circle) or treated with the compound 33 (5 mg/kg—line with square) (Abscissa: Days from 0 to 62 in day; Ordinate: Tumor volume in $mm^3$ from 0 to 2500 (scale 500)).
Figure 7A:
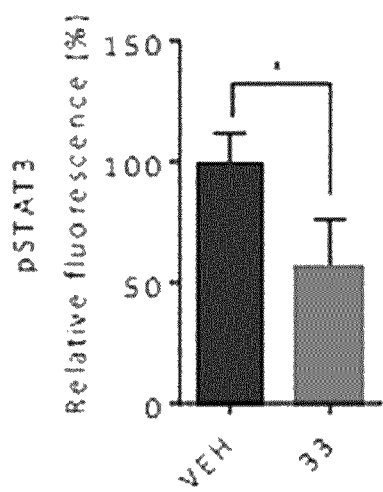
FIG. 7A: Immunofluorescence assay of P-STAT3 (Phosphorylated STAT3) in CT26 cells in Balb/c mice tumors treated with VEH (non-relevant compound which is DMSO) (column on the left) or with compound 33 (column on the right). Histogram plot shows the pSTAT3 relative fluorescence in percentage (Ordinate: pSTAT3 relative fluorescence in percentage). Statistical analysis has been performed by ANOVA (*=$p=0.0019$).
Figure 7B:
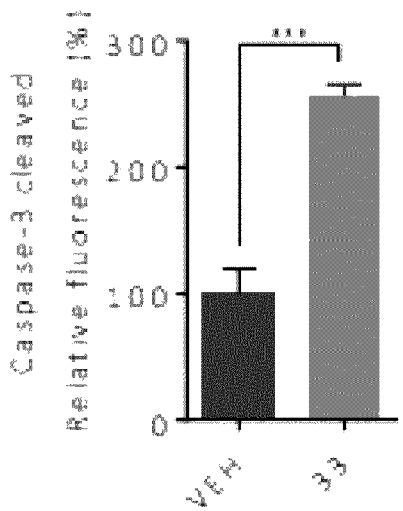
FIG. 7B: Immunofluorescence assay of cleaved caspase-3 (C3C) in CT26 cells in Balb/c mice tumors treated with VEH (column on the left) or with compound 33 (column on the right). Histogram plot shows the Caspase-3 cleaved relative fluorescence in percentage. (Ordinate: Caspase-3 cleaved relative fluorescence in percentage). Statistical analysis has been performed by ANOVA (***=$p=0.0003$)
Figure 7C:
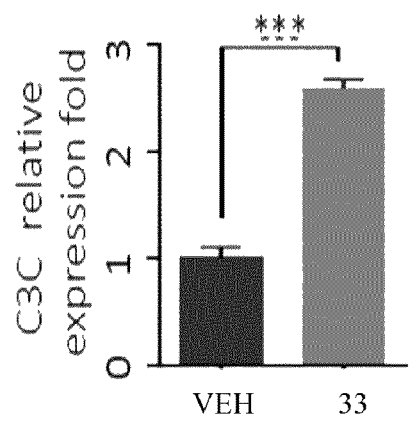
FIG. 7C: Immunofluorescence assay of Cleaved caspase-3 (C3C) in HCT116 from NOD mice tumors treated with VEH (column on the left) or with compound 33 (column on the right). Histogram plot shows the Caspase-3 cleaved relative fluorescence in percentage. (Ordinate: Caspase-3 cleaved relative fluorescence in percentage). Statistical analysis has been performed by ANOVA (***=$p=0.0003$). Scale bar=50 µm.

Two different colorectal mouse models were used: a syngeneic model for which mouse colon cancer CT-26 cells were injected into Balb/c mice and a NOD/SCID model in which mice were implanted with human colorectal cancer HCT116 cells (FIG. 4 A-B). When the tumor reached a size of ~2 mm, mice were treated intraperitoneally with the compound 33 at 5 mg/Kg (BALB/c n=11, NOD SCID n=6) or corn oil 5% DMSO (BALB/c n=10, NOD SCID n=6), every three days until the end of the experiment. The compound 33 was dissolved in DMSO, then diluted 20 times in corn oil (Sigma Aldrich-C8267) and sterilized by filtration with PTFE membrane Millex 0.2 μm (Millipore-SLFG025LS). Tumors were analyzed before reaching 2000 mm3. Treatment by compound 33 induces a decrease in tumor growth of 40% and 60% in the Balb/c and NOD mice, respectively (FIGS. 6A and 6B). Furthermore, these results confirm treatment with compound 33 provoked in the tumor slides a reduction in STAT3 phosphorylation with a percentage of 50% P-STAT3 compared to 100% for the control (FIG. 7A). Compound 33 treatment induced an increase in tumor cell apoptosis, as assessed by analyzing cleaved caspase-3 staining in the tumor slides with a relative expression fold of caspase 3 compared to the control (FIG. 7B and FIG. 7C, for the Balb/c and NOD/SCID model, respectively).

HSP110 protein in the tumor microenvironment negatively affect the anticancer immune response by facilitating the formation of macrophages with an anti-inflammatory profile. The impact of compound 33 treatment on tumor-infiltrating macrophages was then studied on mice models. In particular, the activity of macrophages that encourage inflammation, called M1 macrophages, were analyzed.

In contrast, activity of macrophages that decrease inflammation and encourage tissue repair, called M2 macrophages, were identified. Specific markers of sub-type macrophages (M1 or M2-like macrophages markers) were used, due to their differences in metabolism.

Figure 8A:
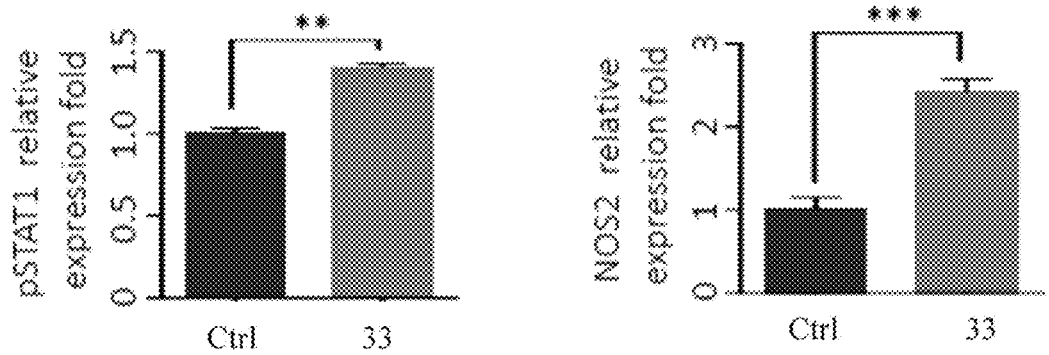
FIG. 8A: Pro-inflammatory M1-like macrophage markers pSTAT1 and NOS2 determined in tumor slides from CT-26-Balb/c mice model. Animals were treated or not every 3 days with the compound 33 (5 mg/Kg) Statistical analysis has been performed by ANOVA (***=$p=0.0051$). The histogram plot shows in ordinate pSTAT1 relative expression fold from 0 to 1.5 (scale bar 0.5) for the histogram on the top left and NOS2 relative expression fold from 0 to 3 (scale bar 1) for the histogram on the top right. First column shows Ctrl and the second one the relative expression for mice treated with compound 33 (for the two histograms).
Figure 8B:
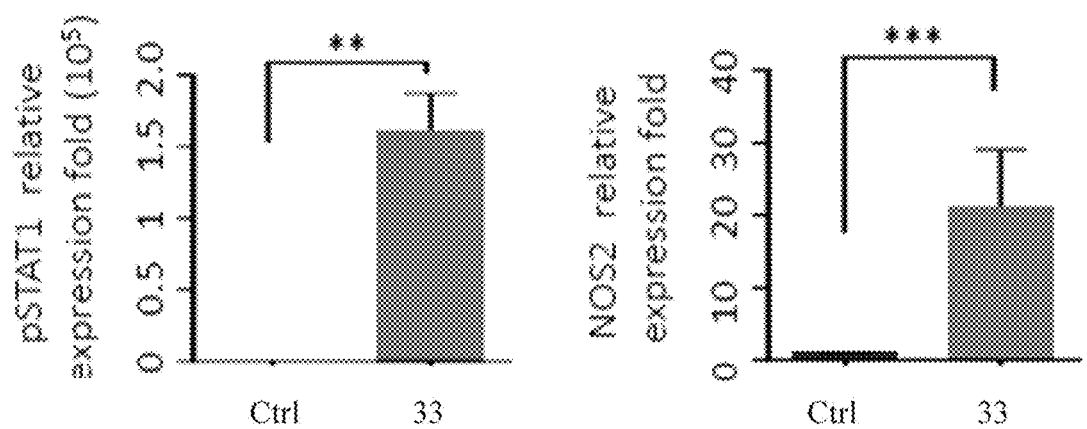
FIG. 8B: Pro-inflammatory M1-like macrophage markers pSTAT1 and NOS2 determined in tumor slides from NOD mice bearing HCT116 xenografts, treated or not with the compound 33) The histogram plot shows in ordinate pSTAT1 relative expression fold from 0 to 2 (scale bar 0.5) for the histogram on the bottom left and NOS2 relative expression fold from 0 to 40 (scale bar 10) for the histogram on the bottom right. First column shows Ctrl and the second one the relative expression for mice treated with compound 33 (for the two histograms). Statistical analysis has been performed by ANOVA (***=$p=0.0019$).

Anti-p-STAT1 (1/200; polyclonal, Cell Signaling), anti-SOCS1 (Suppressor of Cytokine Signaling protein 1, 1/200; polyclonal, Santa Cruz), and anti-NOS2 (Nitric Oxide Synthase 2, 1/200; polyclonal Santa Cruz) antibodies were used for M1-like macrophage markers. Anti-pSTAT6 (1/200; polyclonal Santa Cruz), anti-arginase-1 (1/200; polyclonal Santa Cruz) and anti-ALOX15 (Arachidonate 15-LipOXygenase, 1/200; monoclonal Santa Cruz) antibodies were used for M2-like macrophage markers. Primary antibodies were detected using Alexa fluor 488 or Alexa fluor 568-coupled secondary antibodies (1/500, Invitrogen). Nuclei were stained with 10 μl of ProLong Gold Antifade Mountant with DAPI (Molecular Probes). The same protocol was used for NOD/SCID mice except that mice were killed after 16 days after HCT116 cells injection. For the Balb/c model, mice were sacrificed at day 62 (day 1 being the first day of treatment). The immuno-histochemical analysis in tumor slides both from the Balb/c (syngeneic) and in the NOD/SCID (xenograft) model indicated that compound 33 treatment provoked an increase in the expression of the M1 markers pSTAT1, SOCS1 and NOS2 (FIG. 8 A-B). Especially the pSTAT1 relative expression measured is about 1.5 for compound 33 compared to 1.0 for the control, the NOS2 relative expression measured is about 1 for compound 33 compared to 2.5 for the control (FIG. 8A) in CT-26-Balb/c mice model. The pSTAT1 relative expression measured is about 1.5 for compound 33 compared to 0 for the control and the NOS2 relative expression measured is about 20 for compound 33 compared to 2 for the control (FIG. 8B) in NOD/SCID mice model.

Figure 9A:
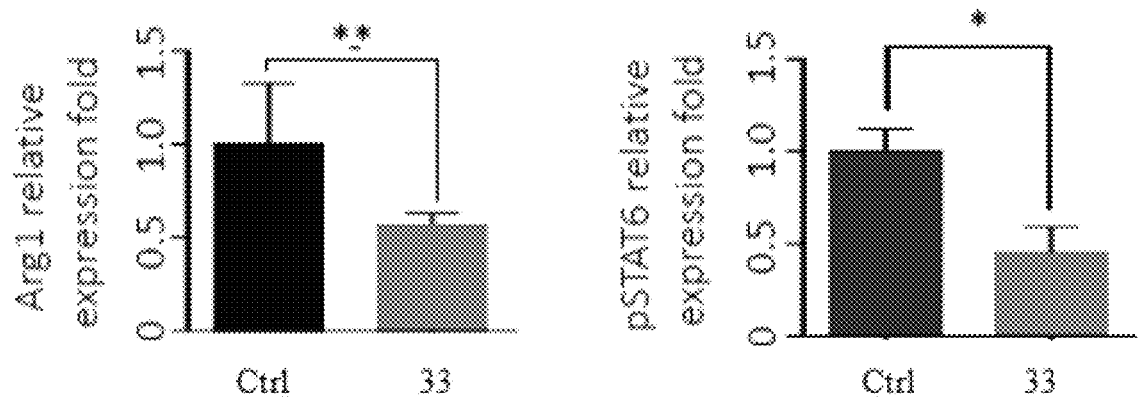
FIG. 9A: Anti-inflammatory macrophage M2-like markers Arg1 and pSTAT6 determined in tumor slides from CT-26-Ballb/c mice model. Animals were treated or not every 3 days with the compound 33 (5 mg/Kg). Statistical analysis has been performed by ANOVA (***=p=0.0031). The histogram plot shows Arg1 relative expression fold from 0 to 1.5 (scale bar 0.5) for the histogram on the top left and pSTAT6 relative expression fold from 0 to 1.5 (scale bar 0.5) for the histogram on the top right. First column shows Ctrl and the second one the relative expression for mice treated with compound 33 (for the two histograms).
Figure 9B:
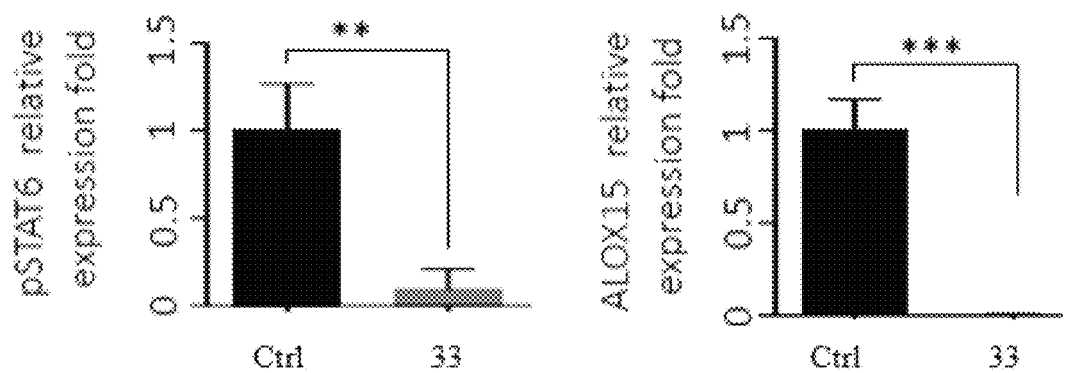
FIG. 9B: M2-like markers pSTAT6 and ALOX15 were determined in tumor slides from NOD mice bearing HCT116 xenografts, treated or not with the compound 33 (related to formula (II)). Statistical analysis has been performed by ANOVA (***: p=0.0481). The histogram plot shows pSTAT6 relative expression fold from 0 to 1.5 (scale bar 0.5) for the histogram on the bottom left and ALOX15 relative expression fold from 0 to 1.5 (scale bar 0.5) for the histogram on the bottom right. First column shows Ctrl and the second one the relative expression for mice treated with compound 33 (for the two histograms).

On the contrary, macrophages M2-like markers such as Arginase1, pSTAT6 and ALOX15 were significantly under expressed in the treated tumors compared to the control mice (FIG. 9 A-B). Especially the Arg1 relative expression measured is about 0.5 for compound 33 compared to 1.0 for the control, the pSTAT6 relative expression measured is about 0.5 for compound 33 compared to 1.0 for the control (FIG. 9A) in CT-26-Balb/c mice model. The pSTAT6 relative expression measured is about 0 for compound 33 compared to 1 for the control and the ALOX15 relative expression measured is about 0 for compound 33 compared to 1 for the control (FIG. 9B) in NOD/SCID mice model.

Altogether, these results suggest that the compounds of the invention may inhibit also the reported function of HSP110 in macrophage polarization, thus favoring an anti-cancer immune response.

Example 3: In Vitro Efficacity of Compounds of Formula (I) Against Human Lymphoma In this example, it is shown that compounds 33 and 52, which inhibit HSP110, abrogate the HSP110/Myd88 interaction which is observed in diffuse large B cell lymphoma cell lines (DLBCL).

MyD88 was immuno-precipitated from the cell line which has been non-treated or treated with the HSP110 inhibitors. Then, HSP110 and MyD88 were revealed by Western Blot. The results are shown in FIG. 10A.

Compound 61 (5061) was used as negative control. The results of FIG. 10A show that compound 61 (5061) does not inhibit the interaction of HSP110 with Myd88.

Further, it has been shown that compound 33 reduces the NFκB signaling pathway (P-p65) and Myd88 expression in two distinct DLBCL cell lines, namely the TMD8 and the HBL1 human diffuse large B-cell lymphoma cell line. The results are shown in FIG. 10B and FIG. 10C, respectively.

As shown in FIG. 10B, compound 33 thus induces the degradation of MyD88.

Further, compounds 33 and 52 lead to a strong decrease of the NFκB signaling pathway (P-p65) in those two distinct DLBCL cell lines, shown by a decrease in IkB phosphorylation (P-IKB) (FIG. 10C).

It has also been shown that compounds 33 and 52 reduce the expression of the anti-apoptotic proteins Bcl2 and Bcl-xL in these two human diffuse large B-cell lymphoma cell lines, as determined by Western blotting after a 76 h in vitro treatment with compound 33 or 52. The results are shown in FIG. 10D.

Also, compound 33 reduces the viability of a plurality of DLBCL cell lines, namely OCI-Ly10 cell line, HBL1 cell line, TMD8 cell line, OCI-Ly3 cell line and U2932 cell line, as determined by Annexin V/7AAD staining after 96 h in vitro treatment with increasing concentrations of compound 33 (=inhibitor 33). Further compound 52 reduces the viability of TMD8 cell line and OCI-Ly3 as determined by Annexin V/7AAD staining after 96 h in vitro treatment with increasing concentrations of compound 52 (=inhibitor 52).

Thus, compounds 33 and 52 induce cell death especially of B-cell lymphoma cells bearing a MyD88 activating mutation, which is not present in the genome of the U2932 cell line. The results are shown in FIG. 10E for compound 33 and FIG. 10F for compound 52.

In addition, it has been observed that compound 52 (=inhibitor 52) reduced the tumor growth of a xenografted DLBCL cell line in mice (FIGS. 11A and 11B, *=p<0.05). Further, no toxicity has been observed associated to the compound 52 at the doses used, as shown by the steady body and spleen weights of the mice during the treatment (FIGS. 11C and 11D).

It has also been shown that compound 33 induces a synergistic effect with another anti-cancer compound, Ibrutinib. Ibrutinib (CAS number 936563-96-1) is a tyrosine kinase inhibitor which is used in the treatment of human lymphomas, with a limited success to date. Thus, beyond being active alone, compound 33, even when used at a suboptimal concentration, is able to potentialize the anti-cancer effect of Ibrutinib, as shown in FIG. 12.

In conclusion, we show that compounds 33 and 52 (=inhibitors 33 and 52) can induce DLBCL cell lines cell death by inhibiting MyD88 and the NFkB pathways in vitro and in vivo (xenograft model) with no apparent toxicity. These molecules are promising drug candidates in DLBCL and potentially other MyD88 and or NFkB-dependent lymphomas. The molecules could be used alone or in association with currently used anticancer drugs in DLBCL such as the Bruton's tyrosine kinase inhibitor Ibrutinib. Indeed, we observe that the compound 33 enhances apoptosis in DLBCL cell lines induced by Ibrutinib.

---

The invention claimed is:

1. A method for treating an individual affected with a HSP110-associated cancer comprising a step of administering to the said individual a compound of formula (I):

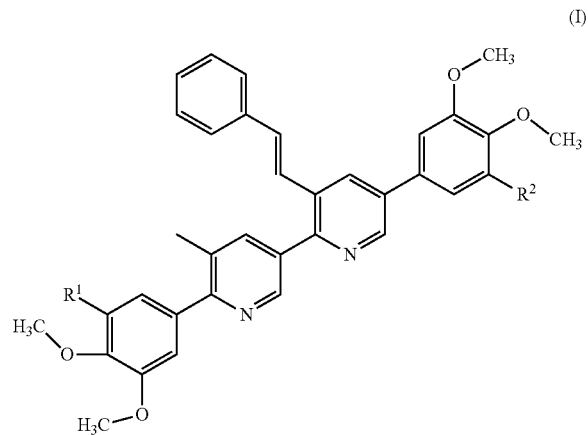

(I)

wherein:
R¹ and R² represent independently a group selected among H and a (C1-C3) alkoxy group;
or one of its pharmaceutically acceptable salts and/or racemic, enantiomeric, diastereoisomeric or tautomeric form,
wherein the HSP110-associated cancer is selected from the group consisting of the colorectal cancer, stomach cancer, endometrial cancer, bladder cancer, urinary tract cancer, ovary cancer, prostate cancer, lymphomas, leukemias, glioblastoma, astrocytoma and neuroblastoma.

2. The method according to claim 1, wherein the HSP110-associated cancer is a cancer for which tumor cell proliferation and/or the absence of tumor cell death is correlated with the activity of HSP110 protein.

3. The method according to claim 1, wherein the HSP110-associated cancer consists of a cancer wherein HSP110 protein is functional for STAT3 phosphorylation (P-STAT3) and/or wherein HSP110 protein maintains anti-aggregation activity, and/or wherein HSP110 protein negatively affects the anticancer immune response.

4. The method according to claim 1, wherein the HSP110-associated cancer consists of a cancer wherein the HSP110 protein is devoid of a HSP110 loss-of-function mutation preventing STAT3 phosphorylation.

5. The method according to claim 1, wherein the HSP110-associated cancer is a cancer wherein the cancer tumor expresses a HSP110 protein that is devoid of one or more mutations in the nucleotide-binding domain of HSP110 protein.

6. The method according to claim 1, wherein the compound is (E)-6'-(3,4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine(formula (III)), or (E)-5,6'-Bis(3,4-dimethoxyphenyl)-5'-methyl-3-styryl-2,3'-bipyridine (formula (IV)), or a mixture thereof.

7. The method according to claim 1, wherein the said compound is combined with one or more additional anti-cancer agents.

8. The method according to claim 1, wherein the said compound is comprised in a composition comprising one or more pharmaceutically acceptable excipients.

9. A method for determining the responsiveness of a cancer patient to a HSP110 inhibitor which is a compound of formula (I) according to claim 1, comprising at least the steps of:
a) determining in a sample previously collected from the said patient the ability of said patient to express a functional HSP110 protein, and
b) selecting the said patient as responsive to a cancer treatment with a HSP110 inhibitor when said HSP110 protein is functional,
wherein the cancer is a HSP110-associated cancer selected from the group consisting of the colorectal cancer, stomach cancer, endometrial cancer, bladder cancer, urinary tract cancer, ovary cancer, prostate cancer, lymphomas, leukemias, glioblastoma, astrocytoma and neuroblastoma.

10. The method according to claim 9, comprising at least the steps of:
a) determining, in a nucleic acid-containing sample previously collected from the said patient, the sequence of the HSP110-encoding nucleic acid, and
b) selecting the said patient as responsive to a cancer treatment with the HSP110 inhibitor when the sequence determined at step a) encodes a HSP110 protein or variant thereof, which induces tumor cell proliferation and/or the absence of tumor cell death.

11. The method according to claim 9, wherein step b) comprises selecting the patient as responsive to a cancer treatment with a HSP110 inhibitor when the sequence determined at step a) encodes a HSP110 protein or variant thereof that is functional for phosphorylating STAT3 protein, and/or if said HSP110 protein maintains anti-aggregation activity, and/or wherein said HSP110 protein negatively affects the anticancer immune response.

12. The method according to claim 9, wherein the HSP110 inhibitor which is a compound of formula (I) is selected from (E)-6'-(3,4-Dimethoxyphenyl)-5'-methyl-3-styryl-5-(3,4,5-trimethoxyphenyl)-2,3'-bipyridine (formula (II)), (E)-5'-Methyl-3-styryl-5,6'-bis(3,4,5-trimethoxyphenyl)-2,3'-bipyridine(formula (III)), (E)-5,6'-Bis(3,4-dimethoxyphenyl)-5'-methyl-3-styryl-2,3'-bipyridine (formula (IV)) and a mixture thereof.

13. The method according to claim 1, wherein the HSP110-associated cancer is a colorectal cancer or a lymphoma.

14. The method according to claim 1, wherein the compound is administered with ibrutinib.

* * * * *